US007956198B2

(12) United States Patent
Sattigeri et al.

(10) Patent No.: US 7,956,198 B2
(45) Date of Patent: Jun. 7, 2011

(54) PHARMACEUTICAL COMPOSITIONS

(75) Inventors: Jitendra A. Sattigeri, Gurgaon (IN); Vinay S. Bansal, New Delhi (IN)

(73) Assignee: Ranbaxy Laboratories, Limited, Haryana (IN)

( * ) Notice: Subject to any disclaimer, the term of this patent is extended or adjusted under 35 U.S.C. 154(b) by 247 days.

(21) Appl. No.: 12/092,930

(22) PCT Filed: Nov. 8, 2006

(86) PCT No.: PCT/IB2006/003152
§ 371 (c)(1),
(2), (4) Date: Jun. 23, 2008

(87) PCT Pub. No.: WO2007/054789
PCT Pub. Date: May 18, 2007

(65) Prior Publication Data
US 2008/0248035 A1    Oct. 9, 2008

(30) Foreign Application Priority Data

Nov. 8, 2005  (IN) ............................ 2964/DEL/2005
Nov. 8, 2005  (IN) ............................ 2967/DEL/2005
Nov. 14, 2005 (IN) ............................ 3033/DEL/2005

(51) Int. Cl.
*C07D 207/00* (2006.01)
(52) U.S. Cl. ........ 548/537; 548/400; 548/530; 514/423; 514/429
(58) Field of Classification Search .................. None
See application file for complete search history.

(56) References Cited

U.S. PATENT DOCUMENTS

| 3,262,977 A | 7/1966 | Harsanyi et al. |
| 3,341,584 A | 9/1967 | Larsen |
| 3,454,635 A | 7/1969 | Weber |
| 3,471,515 A | 10/1969 | Troxler |
| 3,483,221 A | 12/1969 | Wilhelm |
| 3,527,761 A | 9/1970 | Archibald |
| 3,562,257 A | 2/1971 | Kugita |
| 3,576,883 A | 4/1971 | Neuworth |
| 3,642,896 A | 2/1972 | Collin |
| 3,644,353 A | 2/1972 | Lunts et al. |
| 3,649,691 A | 3/1972 | Shavel |
| 3,655,663 A | 4/1972 | Wasson |
| 3,663,570 A | 5/1972 | Sato |
| 3,663,706 A | 5/1972 | Hess et al. |
| 3,669,968 A | 6/1972 | Hess |
| 3,674,836 A | 7/1972 | Creger |
| 3,705,233 A | 12/1972 | Lunts et al. |
| 3,716,583 A | 2/1973 | Nakamura et al. |
| 3,723,446 A | 3/1973 | Scherm et al. |
| 3,773,939 A | 11/1973 | Janssen |
| 3,781,328 A | 12/1973 | Witte |
| 3,850,941 A | 11/1974 | Irikura |
| 3,857,891 A | 12/1974 | Holmes et al. |
| 3,857,952 A | 12/1974 | Wooldridge et al. |
| 3,868,460 A | 2/1975 | Koppe et al. |
| 3,879,554 A | 4/1975 | Temperilli |
| 3,910,924 A | 10/1975 | Tamura et al. |
| 3,912,743 A | 10/1975 | Christensen et al. |
| 3,932,400 A | 1/1976 | Hibino et al. |
| 3,932,645 A | 1/1976 | Meyer et al. |
| 3,934,032 A | 1/1976 | Barrett et al. |
| 3,937,838 A | 2/1976 | Wetterlin et al. |
| 3,948,943 A | 4/1976 | Eberhardt et al. |
| 3,962,238 A | 6/1976 | Mauvernay et al. |
| 3,982,021 A | 9/1976 | Hauck et al. |
| 3,984,413 A | 10/1976 | Metz et al. |
| 3,994,974 A | 11/1976 | Murakami et al. |
| 3,997,666 A | 12/1976 | Witte et al. |
| 3,998,790 A | 12/1976 | Brandstrom et al. |
| 4,011,258 A | 3/1977 | Wetterlin et al. |
| 4,012,444 A | 3/1977 | Lunts et al. |
| 4,032,648 A | 6/1977 | Malen et al. |
| 4,034,009 A | 7/1977 | Zolss et al. |
| 4,051,143 A | 9/1977 | Scherm et al. |
| 4,056,626 A | 11/1977 | Ito et al. |
| 4,058,552 A | 11/1977 | Mieville |
| 4,062,950 A | 12/1977 | Frommer et al. |
| 4,105,776 A | 8/1978 | Ondetti et al. |
| 4,129,565 A | 12/1978 | Fukushima et al. |
| 4,154,839 A | 5/1979 | Wehinger et al. |

(Continued)

FOREIGN PATENT DOCUMENTS

CN     1436174     8/2003

(Continued)

OTHER PUBLICATIONS

Athyros et al. Diabetes Care (2002), vol. 25, pp. 1198-1202.*
U.S. Appl. No. 12/092,813, filed May 6, 2008, Sattigeri et al.
U.S. Appl. No. 10/558,859, filed Nov. 30, 2005, Salman et al.
Allain et al., Clin. Chem., 20:470 (1974).
Baumann et al., "The Convergent Synthesis of CI-981, an Optically Active, Highly Potent, Tissue Selective Inhibitor of HMG-COA Reductase", Tetrahedron Letters, Elsevier, vol. 33, No. 17, Apr. 21, 1992, pp. 2283-2284.

(Continued)

*Primary Examiner* — Patrick T Lewis
(74) *Attorney, Agent, or Firm* — Sheridan Ross, P.C.

(57) ABSTRACT

This invention relates to a combination product or medicament comprising at least one novel substituted pyrrole derivative and one or more dyslipidemic agents, antiobesity agents, antihyperglycaemic agents, anti-inflammatory agents or mixture thereof. Also provided herein are the pharmaceutical compositions comprising at least one novel substituted pyrrole derivative and one or more dyslipidemic agents, antiobesity agents, antihyperglycaemic agents, anti-inflammatory agents or mixture thereof and optionally together with at least one pharmaceutically acceptable carrier, and methods for the treatment or prophylaxis of cardiovascular diseases, Alzheimer's disease, obesity, diabetes or inflammatory diseases comprising administering to a mammal in need thereof therapeutically effective amounts of combination pharmaceutical composition comprising at least one novel substituted pyrrole derivative and one or more dyslipidemic agents, antiobesity agents, antihyperglycaemic agents, anti-inflammatory agents or mixtures thereof.

9 Claims, No Drawings

U.S. PATENT DOCUMENTS

| | | | |
|---|---|---|---|
| 4,182,767 A | 1/1980 | Murai et al. |
| 4,188,390 A | 2/1980 | Campbell |
| 4,217,305 A | 8/1980 | Imai et al. |
| 4,248,883 A | 2/1981 | Sawayama et al. |
| 4,252,721 A | 2/1981 | Silvestrini et al. |
| 4,252,825 A | 2/1981 | Demarne |
| 4,252,984 A | 2/1981 | Manoury et al. |
| 4,258,062 A | 3/1981 | Jonas et al. |
| 4,260,622 A | 4/1981 | Junge et al. |
| 4,264,611 A | 4/1981 | Berntsson et al. |
| 4,310,549 A | 1/1982 | Hajos et al. |
| 4,314,081 A | 2/1982 | Molloy et al. |
| 4,337,201 A | 6/1982 | Petrillo, Jr. |
| 4,344,949 A | 8/1982 | Hoefle et al. |
| 4,410,520 A | 10/1983 | Watthey |
| 4,425,355 A | 1/1984 | Hoefle et al. |
| 4,434,176 A | 2/1984 | Troxler et al. |
| 4,444,779 A | 4/1984 | Kawamatsu et al. |
| 4,448,964 A | 5/1984 | Muto et al. |
| 4,466,972 A | 8/1984 | Neumann |
| 4,470,972 A | 9/1984 | Gold et al. |
| 4,472,380 A | 9/1984 | Harris et al. |
| 4,503,067 A | 3/1985 | Wiedemann et al. |
| 4,508,729 A | 4/1985 | Vincent et al. |
| 4,522,828 A | 6/1985 | Jeffery et al. |
| 4,572,909 A | 2/1986 | Campbell et al. |
| 4,587,258 A | 5/1986 | Gold et al. |
| 4,598,089 A | 7/1986 | Hadvary et al. |
| 4,663,325 A | 5/1987 | Ohtaka et al. |
| 4,672,068 A | 6/1987 | Kutsuma et al. |
| 4,681,893 A | 7/1987 | Roth |
| 4,687,777 A | 8/1987 | Meguro et al. |
| 4,699,905 A | 10/1987 | Yanagisawa et al. |
| 4,701,559 A | 10/1987 | Horii et al. |
| 4,705,797 A | 11/1987 | Nardi et al. |
| 4,731,478 A | 3/1988 | Niigata et al. |
| 4,734,280 A | 3/1988 | Braquet |
| 4,801,599 A | 1/1989 | Semeraro et al. |
| 4,822,818 A | 4/1989 | Oka et al. |
| 4,873,259 A | 10/1989 | Summers, Jr. et al. |
| 4,879,303 A | 11/1989 | Davison et al. |
| 4,994,461 A | 2/1991 | Ulrich |
| 5,002,953 A | 3/1991 | Hindley |
| 5,049,559 A | 9/1991 | Braquet et al. |
| 5,128,355 A | 7/1992 | Carini et al. |
| 5,155,103 A | 10/1992 | Weber et al. |
| 5,155,120 A | 10/1992 | Lazar et al. |
| 5,185,351 A | 2/1993 | Finkelstein et al. |
| 5,273,995 A | 12/1993 | Roth |
| 5,274,094 A | 12/1993 | Whittaker et al. |
| 5,344,914 A | 9/1994 | Gibson et al. |
| 5,349,056 A | 9/1994 | Panayotatos |
| 5,356,896 A | 10/1994 | Kabadi et al. |
| 5,385,929 A | 1/1995 | Bjorge et al. |
| 5,399,578 A | 3/1995 | Buhlmayer et al. |
| 5,422,351 A | 6/1995 | Piwinski et al. |
| 5,424,286 A | 6/1995 | Eng |
| 5,466,823 A | 11/1995 | Talley et al. |
| 5,474,995 A | 12/1995 | Ducharme et al. |
| 5,491,172 A | 2/1996 | Lee et al. |
| 5,492,906 A | 2/1996 | Braquet et al. |
| 5,510,332 A | 4/1996 | Kogan et al. |
| 5,541,183 A | 7/1996 | Park et al. |
| 5,552,438 A | 9/1996 | Christensen, IV |
| 5,559,233 A | 9/1996 | Bernhart et al. |
| 5,624,941 A | 4/1997 | Barth et al. |
| 5,633,272 A | 5/1997 | Talley et al. |
| 5,693,675 A | 12/1997 | Mandeville, III et al. |
| 5,712,298 A | 1/1998 | Amschler |
| 5,733,931 A | 3/1998 | Yamada et al. |
| 5,744,501 A | 4/1998 | Norden |
| 5,753,653 A | 5/1998 | Bender et al. |
| 5,767,115 A | 6/1998 | Rosenblum et al. |
| 5,932,598 A | 8/1999 | Talley et al. |
| 5,968,982 A | 10/1999 | Voss et al. |
| 5,985,322 A | 11/1999 | Anderson et al. |
| 5,990,173 A | 11/1999 | Patoiseau et al. |
| 5,994,510 A | 11/1999 | Adair et al. |
| 6,015,557 A | 1/2000 | Tobinick et al. |
| 6,147,090 A | 11/2000 | DeNinno et al. |
| 6,197,786 B1 | 3/2001 | DeNinno et al. |
| 6,268,392 B1 | 7/2001 | Keller et al. |
| 6,329,336 B1 | 12/2001 | Bridon et al. |
| 6,329,344 B1 | 12/2001 | Arora et al. |
| 6,395,751 B1 | 5/2002 | DeNinno et al. |
| 6,420,417 B1 | 7/2002 | Keller et al. |
| 6,426,365 B1 | 7/2002 | Shinkai et al. |
| 6,489,478 B1 | 12/2002 | DeNinno et al. |
| 6,511,985 B1 | 1/2003 | Ippen et al. |
| 6,534,088 B2 | 3/2003 | Guivarc'h et al. |
| 6,569,461 B1 | 5/2003 | Tilyer et al. |
| 6,586,448 B1 | 7/2003 | DeNinno et al. |
| 6,590,085 B1 | 7/2003 | Arora et al. |
| 6,642,268 B2 | 11/2003 | Keller et al. |
| 6,753,346 B2 | 6/2004 | Shinkai et al. |
| 6,787,570 B2 | 9/2004 | Sikorski et al. |
| 6,794,396 B2 | 9/2004 | Lee et al. |
| 6,803,388 B2 | 10/2004 | Sikorski et al. |
| 6,884,226 B2 | 4/2005 | Pereira |
| 6,992,194 B2 | 1/2006 | Lidor-Hadas et al. |
| 7,056,936 B2 | 6/2006 | Kilian et al. |
| 7,361,772 B2 | 4/2008 | Mathew et al. |
| 2002/0052312 A1 | 5/2002 | Reiss et al. |
| 2002/0183378 A1 | 12/2002 | Aronhime et al. |
| 2003/0153617 A1 | 8/2003 | Dalen et al. |
| 2004/0029962 A1 | 2/2004 | Chen et al. |
| 2004/0053842 A1 | 3/2004 | Nguyen et al. |
| 2004/0097555 A1 | 5/2004 | Ohkawa et al. |
| 2004/0102511 A1 | 5/2004 | Sattigeri et al. |
| 2004/0132771 A1 | 7/2004 | Babcock et al. |
| 2005/0032878 A1 | 2/2005 | Deboeck et al. |
| 2005/0063911 A1 | 3/2005 | Nilsson et al. |
| 2005/0187204 A1 | 8/2005 | Kondo |
| 2007/0238716 A1 | 10/2007 | Murthy et al. |
| 2007/0259874 A1 | 11/2007 | Palle et al. |
| 2008/0153896 A1 | 6/2008 | Yadav et al. |
| 2008/0287690 A1 | 11/2008 | Kaul et al. |

FOREIGN PATENT DOCUMENTS

| | | |
|---|---|---|
| EP | 0247633 | 12/1987 |
| EP | 0409281 | 1/1991 |
| EP | 0419049 | 3/1991 |
| EP | 0542355 | 5/1993 |
| EP | 0542356 | 5/1993 |
| EP | 0606646 | 7/1994 |
| EP | 0651739 | 5/1995 |
| EP | 0680963 | 11/1995 |
| EP | 0753298 A1 | 1/1997 |
| EP | 0818197 | 1/1998 |
| EP | 0818448 | 1/1998 |
| EP | 0842943 | 5/1998 |
| EP | 0903353 | 3/1999 |
| EP | 0905139 | 3/1999 |
| EP | 0918059 | 5/1999 |
| EP | 1488808 A | 12/2004 |
| EP | 1510208 | 3/2005 |
| EP | 1523316 | 4/2005 |
| RU | 2279430 | 7/2006 |
| UA | 72290 | 9/2002 |
| WO | WO 95/15973 | 6/1995 |
| WO | WO 95/28926 | 11/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/31206 | 10/1996 |
| WO | WO 96/40641 | 12/1996 |
| WO | WO 96/40781 | 12/1996 |
| WO | WO 97/02289 | 1/1997 |
| WO | WO 97/03094 | 1/1997 |
| WO | WO97/16184 A | 5/1997 |
| WO | WO 97/22619 | 6/1997 |
| WO | WO 98/19998 | 5/1998 |
| WO | WO 98/27098 | 6/1998 |
| WO | WO 98/47892 | 10/1998 |
| WO | WO 98/53814 | 12/1998 |
| WO | WO 98/53817 | 12/1998 |

| WO | WO 98/53818 | 12/1998 |
| --- | --- | --- |
| WO | WO 98/54207 | 12/1998 |
| WO | WO 99/11259 | 3/1999 |
| WO | WO99/20110 A | 4/1999 |
| WO | WO 99/23063 | 5/1999 |
| WO | WO 99/24398 | 5/1999 |
| WO | WO 99/35163 | 7/1999 |
| WO | WO 99/36393 | 7/1999 |
| WO | WO 99/37605 | 7/1999 |
| WO | WO 99/37618 | 7/1999 |
| WO | WO 99/43642 | 9/1999 |
| WO | WO99/47138 A | 9/1999 |
| WO | WO 99/47547 | 9/1999 |
| WO | WO 99/54321 | 10/1999 |
| WO | WO99/58505 A | 11/1999 |
| WO | WO 99/58902 | 11/1999 |
| WO | WO 99/61465 | 12/1999 |
| WO | WO 99/67230 | 12/1999 |
| WO | WO 00/00477 | 1/2000 |
| WO | WO 00/01690 | 1/2000 |
| WO | WO 00/05223 | 2/2000 |
| WO | WO 00/05224 | 2/2000 |
| WO | WO 00/15612 | 3/2000 |
| WO | WO 00/18759 | 4/2000 |
| WO | WO 00/18760 | 4/2000 |
| WO | WO 00/35425 | 6/2000 |
| WO | WO 00/43384 | 7/2000 |
| WO | WO 01/13953 | 3/2001 |
| WO | WO 01/32127 | 5/2001 |
| WO | WO01/37831 A | 5/2001 |
| WO | WO 01/42246 | 6/2001 |
| WO | WO 01/53257 | 7/2001 |
| WO | WO 01/93860 | 12/2001 |
| WO | WO 01/96311 | 12/2001 |
| WO | WO 02/13797 | 2/2002 |
| WO | WO 02/43732 | 6/2002 |
| WO | WO 02/051804 | 7/2002 |
| WO | WO 02/096422 | 12/2002 |
| WO | WO03/007993 A | 1/2003 |
| WO | WO 03/013607 | 2/2003 |
| WO | WO 03/013608 | 2/2003 |
| WO | WO 03/066063 | 8/2003 |
| WO | WO03/077896 A | 9/2003 |
| WO | WO 03/080070 | 10/2003 |
| WO | WO 03/088962 | 10/2003 |
| WO | WO03/094923 A | 11/2003 |
| WO | WO 2004/004777 | 1/2004 |
| WO | WO 2004/004778 | 1/2004 |
| WO | WO 2004/014896 | 2/2004 |
| WO | WO 2004/019985 | 3/2004 |
| WO | WO2004/028456 A | 4/2004 |
| WO | WO 2004/039373 | 5/2004 |
| WO | WO 2004/056359 | 7/2004 |
| WO | WO2004/056395 A | 7/2004 |
| WO | WO2004/062557 A | 7/2004 |
| WO | WO 2004/067006 | 8/2004 |
| WO | WO 2004/098583 | 11/2004 |
| WO | WO2004/106299 A2 | 12/2004 |
| WO | WO 2005/009340 | 2/2005 |
| WO | WO2005/014539 A | 2/2005 |
| WO | WO 2005/018626 | 3/2005 |
| WO | WO 2005/021515 | 3/2005 |
| WO | WO 2005/026163 | 3/2005 |
| WO | WO 2005/034908 | 4/2005 |
| WO | WO 2005/041864 | 5/2005 |
| WO | WO 2005/051931 | 6/2005 |
| WO | WO 2005/056536 | 6/2005 |
| WO | WO 2005/058813 | 6/2005 |
| WO | WO 2005/058898 | 6/2005 |
| WO | WO 2005/100318 | 10/2005 |
| WO | WO 2005/100331 | 10/2005 |
| WO | WO 2006/085212 | 8/2006 |
| WO | WO 2006/117743 | 11/2006 |
| WO | WO 2007/054789 | 5/2007 |
| WO | WO 2007/054790 | 5/2007 |
| WO | WO 2007/054896 | 5/2007 |

OTHER PUBLICATIONS

Bedford et al., "Nonquaternary Cholinesterase Reactivators. 3. 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", Journal of Medicinal Chemistry, 29(11):2174-2183 (1986).

Cui et al., J. Biol. Chem., 278:10214-10220 (2003).

Dolinsky et al., Biochem. J., 378:967-974 (2004).

Frederikson et al., J. Lipid Res., 45:592-601 (2004).

Friedewald et al., Clin. Chem., 18:6, pp. 499-502 (1972).

Frings et al., Clin. Chem., 18(7), pp. 673-674 (1972).

Fujino et al., "Metabolic properties of the acid and lactone froms of HMG-CoA reductasse inhibitors", Xenobiotica, Nov./Dec. 2004, vol. 34, No. 11/12, pp. 961-971.

Harwood et al., J. Lipid Res., 34:377-395 (1993).

Heller et al., "Solubilization and Partial Purification of Hepatic 3-Hydroxy-3Methylglutaryl Coenzyme A Reductase," Biochemical and Biophysical Research Communications, 50(3):859-865 (1973).

Kubo and Strott, "Differential Activity of 3-Hydroxy-3-Methylglutaryl Coenzyme A Reductase in Zones of the Adrenal Cortex," Endocrinology, 120(1):214-221 (1987).

Lorenzen et al., Mol. Pharmacol., 59:349-357 (2001).

Meyer et al., "Annulation of a,b-Unsaturated Ketones by a Micael Addition-Cyclization Sequence. A Versatile Syntesis of Alicyclic Six-Membered Rings", Journal of Organice Chemistry, 50(4):438-447 (1985).

Renodon-Corniere et al., "N-Aryl N'Hydroxyguanidines, A New Class of NO-Donors after Selective Oxidation by Nitric Oxide Synthases: Structure-Activity Relationship," Journal of Medicinal Chemistry, 45(4):944-954 (2002).

Rifai et al., Clin. Chem., 32(6):957-961 (1986).

Sampson et al., Clin. Chem., 47(3):532-539 (2001).

Shefer et al., J. Lipid Res., 22:532-536 (1981).

Sun et al., "A general Sythesis of dioxolenone prodrug moieties", Tetrahedron Letters, 43:1161-1164 (2002).

U.S. Appl. No. 60/498,947, filed Aug. 29, 2003, entitled "Isoxazoline derivatives as inhibitors or phophodiesterase type-IV".

International Preliminary Report on Patentability for International (PCT) Patent Application No. PCT/IB2006/003152, issued May 14, 2008.

Patani et al., "Bioisosterism: A Rational Approach in Drug Design," Chem. Rev., 1996, vol. 96, pp. 3147-3176.

Giron, "Investigations of Polymorphism and Pseudo-Polymorphism in Pharmaceuticals by Combined Thermoanalytical Techniques," J. Therm. Anal. Cal., 2001, vol. 64, pp. 37-60.

Giron, "Applications of Thermal Analysis and Coupled Techniques in Pharmaceutical Industry," J. Therm. Anal. Cal., 2002, vol. 68, pp. 335-357.

Rodriguez-Spong et al., "General principles of pharmaceutical solid polymorphism: a supramolecular perspective," Advanced Drug Delivery Reviews, 2004, vol. 56, pp. 241-274.

Souiliac et al., "Characterization of Delivery Systems, Differential Scanning Calorimetry," pp. 217-218 (in Encyclopedia of Controlled Drug Delivery, 1999, John Wiley & Sons, pp. 212-227).

Rautio et al., "Prodrugs: design and clinical applications," Nature Reviews Drug Discovery, 2008, vol. 7, pp. 255-270.

Wang et al., "Drug Delivery: Principles and Applications," John Wiley & Sons, Inc. Publication, 2005, Section 8.3, pp. 136-137.

Smith, "Do prodrugs deliver?" Current Opinion in Drug Discovery & Development, 2007, vol. 10, pp. 550-559.

Testa, "Prodrugs: bridging pharmacodynamic/pharmacokinetic gaps," Current Opinion in Chemical Biology, 2009, vol. 13, pp. 338-344.

Fura, A., "Role of pharmacologically active metabolites in drug discovery and development," DDT, Feb. 2006, vol. 11, pp. 133-142.

Anari et al., "Bridging cheminformatic metabolite prediction and tandem mass spectrometry," DDT, May 2005, vol. 10, pp. 711-717.

Nedderman, "Metabolites in Safety Testing: Metabolite Identification Strategies in Discovery and Development," Biopharm. Drug Dispos., 2009, vol. 30, pp. 152-162.

"Prevent" definition from dictionary.com, accessed Nov. 28, 2007.

Carr et al., "Enzymatic Determination of Triglyceride, Free Cholesterol, and Total Cholesterol in Tissue Lipid Extracts", Clin. Biochem., 26:39-42 (1993).

Ruys et al., "The Estimation of Serum Triglycerides by Nephelometry: A Simple Method for the Estimation of Serum Triglycerides Suitable for the Small Laboratory", Med. J. Aust., 22(1):385-387 (1975).

Niculescu-Duvaz D et al., "Self-Immolative Nitrogen Mustard Profdrugs for Suicide Gene Therapy", J. Med. Chem. 41(26):5297-5309 (1998).

Nakanishi, K., "Terpene trilactones from Gingko bioloba: From ancient times to the 21st century", Bioorg. Med. Chem., 13:4987-5000 (2005).

Rinaldi-Carmona et al., "Biochemical and Pharmacological Characterisation of SR141716A, the first potent and selective brain cannabinoid receptor antagonist", Life Sci., 56:1941-1947 (1995).

Rodriguez-Sureda et al., "A Procedure for measuring triacylglyceride and cholesterol content using a small amount of tissue", Anal. Biochem., 343:277-282 (2005).

Karimi et al., "Lithium triflate (LiOTf) catalyzed efficient and chemoselective tetrahydropyranylation of alcohols and phenols under mild and neutral reaction conditions", Tetrahedron Lett., 43(30):5353 (2002).

Wilson et al., "Estimation of VLDL cholesterol in hyperlipidemia", Clin. Chim. Acta., Oct. 15; 1513:285-291 (1985).

Zhang et al., "Niacin mediates lipolysis in adipose tissue through its G-protein coupled receptor HM74A", Biochem and Biophys. Res. Commun., 334:729-732 (2005).

International Search Report for International (PCT) Patent Application No. PCT/IB2006/003152, mailed Apr. 3, 2007.

Examination Report for New Zealand Patent Application No. 567738, dated Feb. 12, 2010.

First Office Action for Chinese Patent Application No. 200680041614.8, dispatched on Feb. 12, 2010.

International Search Report prepared by the European Patent Office dated Mar. 22, 2007, for International Application No. PCT/IB2006/003152; Applicant, Ranbaxy Laboratories Limited.

Written Opinion prepared by the European Patent Office dated Mar. 22, 2007, for International Application No. PCT/IB2006/003152; Applicant, Ranbaxy Laboratories Limited.

Anderson, "Chapter 10: Work-up," in Practical Process Research & Development, 2000, pp. 203-221.

Bravo, et al., "Prevalence of Potentially Severe Drug-Drug Interactions in Ambulatory Patients with Dyslipidaemia Receiving HMG-CoA Reductase Inhibitor Therapy," Drug Safety 2005: 28(3):263-275.

Byrn et al., "Chapter 11: Hydrates and Solvates," Solid-State Chemistry of Drugs (2nd Ed.), 1999, pp. 233-247.

Morissette et al., "High-throughput crystallization: polymorphs, salts, co-crystals and solvates of pharmaceutical solids," Adv. Drug Delivery Rev. 2004, vol. 56, pp. 275-300.

Wilke, et al., "Relative impact of CYP3A genotype and concomitant medication on the severity of atorvastatin-induced muscle damage," Pharmacogenetics and Genomics 2005, 15(6):415-421.

Translation of Office Action for Russian Federation National Phase Application No. 2008122455/15, received from foreign counsel on Sep. 10, 2010.

Brittain, ed., Polymorphism in Pharmaceutical Solids, vol. 95, 1999, Taylor & Francis, pp. 1-219.

Byrn et al., "Pharmaceutical Solids: A Strategic Approach to Regulatory Considerations," Pharmaceutical Research, 1995, vol. 12, No. 7, pp. 945-954.

Official Action (including translation) for Chinese Patent Application No. 200680041614.8, mailed Nov. 1, 2010.

* cited by examiner

PHARMACEUTICAL COMPOSITIONS

CROSS REFERENCE TO RELATED APPLICATIONS

This application is a national stage application under 35 U.S.C. 371 of PCT Application No. PCT/IB2006/003152 having an international filing date of Nov. 8, 2006, which designated the United States, which PCT application claimed the benefit of Indian Application Serial No. 2964/DEL/2005, filed Nov. 8, 2005; Indian Application Serial No. 2967/DEL/2005, filed Nov. 8, 2005 and Indian Application Serial No. 3033/DEL/2005, filed Nov. 14, 2005, the entire disclosure of each of these priority documents is incorporated herein by reference.

FIELD OF THE INVENTION

This invention relates to a combination product or medicament comprising at least one novel substituted pyrrole derivative and one or more dyslipidemic agents, antiobesity agents, antihyperglycaemic agents, anti-inflammatory agents or mixtures thereof. Also provided herein are pharmaceutical compositions comprising at least one novel substituted pyrrole derivative and one or more dyslipidemic agents, antiobesity agents, antihyperglycaemic agents, anti-inflammatory agents or mixture thereof and optionally together with at least one pharmaceutically acceptable carrier. Also provided herein are methods for the treatment or prophylaxis of cardiovascular diseases, Alzheimer's disease, obesity, diabetes or inflammatory diseases comprising administering to a mammal in need thereof therapeutically effective amounts of combination pharmaceutical composition comprising at least one novel substituted pyrrole derivative and one or more dyslipidemic agents, antiobesity agents, antihyperglycaemic agents, anti-inflammatory agents or mixtures thereof.

BACKGROUND OF THE INVENTION

Cardiovascular disease and its associated maladies, dysfunctions and complications are a principal cause of disability and the chief cause of death. One specific factor significantly contributing to this pathophysiologic process is atherosclerosis, which has been generally recognized as the leading health care problem both with respect to mortality and health care costs.

Atherosclerosis is characterized by the deposition of fatty substances, primarily cholesterol, resulting in plaque formation on the inner surface of the arterial wall and degenerative change to the arteries.

It is now well established that cardiovascular disorders including myocardial infarction, coronary heart disease, hypertension and hypotension, cerebrovascular disorders including stroke, cerebral thrombosis and memory loss due to stroke; peripheral vascular disease and intestinal infarction are caused by blockage of arteries and arterioles by atherosclerotic plaque. Atherosclerotic plaque formation is multifactorial in its production. Numerous studies have demonstrated that a low plasma concentration of high-density lipoprotein (HDL) cholesterol is a powerful risk factor for the development of atherosclerosis. HDL is one of the major classes of lipoproteins that function in the transport of lipids through the blood. The major lipids found associated with HDL include cholesterol; cholesteryl ester, triglycerides, phospholipids and fatty acids. The other classes of lipoproteins found in the blood are low density lipoprotein (LDL), intermediate density lipoprotein (IDL), and very low density lipoprotein (VLDL). Since low levels of HDL cholesterol increase the risk of atherosclerosis, method for elevating plasma HDL cholesterol would be beneficial for the treatment of atherosclerosis and other diseases associated with the accumulation of lipid in the blood vessels.

Combination therapies for the treatment of diseases, which are affected by low levels of HDL-cholesterol and/or high levels of LDL-cholesterol and triglycerides, for example, atherosclerosis and cardiovascular diseases, have been described in the literature. For example, U.S. Pat. No. 6,586,448 discloses pharmaceutical combination compositions comprising CETP inhibitor and other therapeutic agents, for example, HMG-COA reductase inhibitor, a PPAR agonist or fibrate, for the treatment of diseases which are exacerbated by low levels of HDL cholesterol and/or high levels of LDL-cholesterol and triglycerides. U.S. Pat. No. 6,462,091 discloses combinations of CETP inhibitor and HMG-COA reductase inhibitor for cardiovascular indications. Combinations of CETP inhibitor and HMG-COA reductase inhibitor have also been disclosed in PCT publication Nos. WO 04/004778, WO 04/056359 or WO 04/098583; U.S. Patent application Nos. 20040053842 or 20040132771. U.S. Pat. No. 6,534,088 discloses combinations of HMG-COA reductase inhibitor and fibrate for treatment of patients with dyslipidemia, hyperlipidemia, hypercholesterolemia and related conditions. Combinations of fibrate and HMG-COA reductase inhibitor have also been disclosed in U.S. Pat. No. 6,511,985; PCT Publication Nos. WO 2005/034908, WO 03/013607, WO 01/37831. U.S. Pat. No. 6,420,417 discloses combinations of ileal bile acid transport inhibiting benzothiepines and HMG-COA reductase inhibitors for treating hyperlipidemic conditions. Combinations of ileal bile acid transport inhibitor and HMG-COA reductase inhibitor have also been disclosed in U.S. Pat. Nos. 6,642,268 and 6,268,392. PCT Publication No. WO 03/080070 discloses combinations of HMG-COA reductase inhibitor and insulin secretion enhancer or insulin sensitizer. Other references describing such combinations are European Patent Application No. 0753298, 1510208, 1523316; PCT Publication No. WO 2005/018626. PCT Publication No. WO 03/088962 discloses combination therapy using a PPAR agonist and other therapeutic agents, for example, HMG-COA reductase inhibitor, a bile acid sequestrant or CETP inhibitor. Other references disclosing such combinations are PCT Publication No. 03/013608; U.S. Patent application No. 2005/0032878. PCT Publication No. WO 04/004777 discloses CETP inhibitors and antihypertensive agents as well as optionally HMG-COA reductase inhibitors.

Inflammatory diseases are all characterized by the presence of mediators that recruit and activate different inflammatory cells which release enzymes or oxygen radicals causing symptoms, the persistence of inflammation and when chronic, destruction or disruption of normal tissue.

Combination therapies for the treatment of inflammatory diseases have been described in the literature. For example, U.S. Patent Publication No. 2002/0052312A1 discloses combination therapy of chronic obstructive pulmonary disease using muscarinic receptor antagonists in combination with beta.2-agonist, antitussive, corticosteroid, decongestant, histamine H1 antagonist (antihistamine), dopamine antagonist, leukotriene antagonist, 5-lipooxygenase inhibitor, phosphodiesterase IV inhibitor, VLA-4 antagonist, and theophylline. PCT Publication No. WO 2005/009340 describes methods for the treatment or prevention of respiratory disorders with a cycloxygenase-2 inhibitor in combination with a muscarinic receptor antagonist and compositions thereof. U.S. Publication No. 2005/0063911 discloses combined doses of Formoterol and an anticholinergic agent. PCT Publication No. WO 04/019985 discloses pharmaceutical products and compositions comprising specific anticholinergic agents, beta-2 agonists and corticosteriods. PCT Publication No. WO 02/096422 discloses combinations of a dopamine D2-receptor agonist and tiotropium or a derivative thereof for treating obstructive airways and other inflammatory diseases. PCT Publication No. WO 03/066063 discloses pharmaceutical compositions comprising 17alpha-furanylesters of 17beta-carbothiate androstanes with a muscarinic receptor antagonists. U.S. Publication No. 2004/0097555 discloses pharmaceutical agents comprising one or more kinds of a p38 MAP kinase inhibitor and/or a TNF-alpha production inhibitor and one or more kinds of drugs selected from (1) a non-steroidal anti-inflammatory drug, (2) a disease-modifying anti-rheumatic drug, (3) an-anti-cytokine drug, (4) an immunomodulator, (5) a steroid and (6) a c-Jun N-terminal kinase inhibitor in combination, which has been said to be useful as a prophylactic or therapeutic agent of the diseases rheumatism, arthritis and other diseases. PCT Publication No. WO 95/28926 discloses a pharmaceutical composition for treating multiple sclerosis comprising an effective amount of a combination of a PDE IV inhibitor and an anti-inflammatory or immunomodulatory drug in a pharmaceutically acceptable carrier. PCT Publication No. WO 01/13953 and U.S. Publication No. 20040034087 disclose the combined administration of PDE inhibitors and beta 2 adrenoceptor agonists for the treatment of respiratory tract disorders. PCT Publication No. WO 01/32127 discloses the treatment of pulmonary diseases such as chronic obstructive pulmonary disease or asthma by administering a phosphodiesterase 4 inhibitor in combination with anti-inflammatory corticosteroid. PCT Publication No. WO 2004/067006 discloses treatments and methods for PDE IV-related conditions and for TNF-alpha-related conditions using a combination of a PDE IV inhibitor and a TNF-alpha antagonist. PCT Publication No. WO 2005/041864 discloses a method for the prevention and/or treatment of respiratory inflammation, and in particular asthma and COPD, in a subject in need of such prevention or treatment, the method comprising administering to the subject a cycloogenase-2 inhibitor in combination with a phosphodiesterase 4 inhibitor.

Despite the existence of such combinations for the treatment or prophylaxis of cardiovascular diseases or inflammatory diseases, there remains a need for safe and effective combination products or medicaments for the treatment or prophylaxis of cardiovascular diseases or inflammatory diseases.

SUMMARY OF THE INVENTION

Provided herein are combination products or medicaments comprising at least one novel substituted pyrrole derivative, and one or more dyslipidemic agents, antiobesity agents, antihyperglycaemic agents, anti-inflammatory agents, or mixtures thereof for treating or prophylaxis of cardiovascular diseases, Alzheimer's disease, obesity diabetes or inflammatory diseases.

Also provided herein is a pharmaceutical composition comprising a) therapeutically effective amounts of at least one substituted pyrrole derivative, optionally together with at least one pharmaceutically acceptable carrier, and b) therapeutically effective amounts of one or more dyslipidemic agents, antiobesity agents, antihyperglycaemic agents, anti-inflammatory agents or mixtures thereof, optionally together with at least one pharmaceutically acceptable carrier.

Also provided herein is a single pharmaceutical composition comprising at least one substituted pyrrole derivative, and one or more dyslipidemic agents, antiobesity agents, antihyperglycaemic agents, anti-inflammatory agents or mixtures thereof, and optionally together with at least one pharmaceutically acceptable carrier.

Also provided herein are pharmaceutical packages comprising single compositions comprising therapeutically effective amounts of at least one substituted pyrrole derivative, and one or more dyslipidemic agents, antiobesity agents, antihyperglycaemic agents, anti-inflammatory agents or mixtures thereof, optionally together with at least one pharmaceutically acceptable carrier.

Also provided herein are pharmaceutical packages comprising a first pharmaceutical composition comprising therapeutically effective amounts of at least one substituted pyrrole derivative, optionally together with at least one pharmaceutically acceptable carrier; and a second pharmaceutical composition comprising one or more dyslipidemic agents, antiobesity agents, antihyperglycaemic agents, anti-inflammatory agents or mixtures thereof, optionally together with at least one pharmaceutically acceptable carrier. The separate compositions can be given separately, simultaneously or sequentially.

Also provided herein are pharmaceutical kits containing a single composition comprising therapeutically effective amounts of at least one substituted pyrrole derivative, and one or more dyslipidemic agents, antiobesity agents, antihyperglycaemic agents, anti-inflammatory agents or mixtures thereof, optionally together with at least one pharmaceutically acceptable carrier, prescribing information and a container.

Also provided herein are pharmaceutical kits containing a first pharmaceutical composition of at least one substituted pyrrole derivative, optionally together with at least one pharmaceutically acceptable carrier; a second pharmaceutical composition of one or more dyslipidemic agents, antiobesity agents, antihyperglycaemic agents, anti-inflammatory agents or mixtures thereof, optionally together with at least one pharmaceutically acceptable carrier; prescribing information and a container. These separate compositions can be used simultaneously, separately or sequentially.

Also provided herein are methods for the treatment or prophylaxis of cardiovascular diseases, Alzheimer's disease, obesity, diabetes or inflammatory diseases comprising administering to a mammal in need thereof therapeutically effective amounts of any of the above-described combination pharmaceutical compositions, including, for example, these comprising at least one substituted pyrrole derivative and one or more dyslipidemic agents, antiobesity agents, antihyperglycaemic agents, anti-inflammatory agents or mixtures thereof.

Other aspects will be set forth in accompanying detailed description, which follows and in the part will be apparent from the description or may be learnt by the practice of the invention. However, it should be understood that the following detailed description is given by way of illustration only since various changes and modifications within the spirit and scope of the invention will become apparent to those skilled in the art and are encompassed within the scope of this invention.

DETAILED DESCRIPTION OF THE INVENTION

The combination product or medicament, pharmaceutical composition, pharmaceutical package, pharmaceutical kit and method for treatment or prophylaxis of cardiovascular diseases, Alzheimer's disease, obesity, diabetes or inflammatory diseases involve therapeutically effective amounts of at least one substituted pyrrole derivative and one or more dyslipidemic agents, antiobesity agents, antihyperglycaemic agents, anti-inflammatory agents or mixtures thereof.

Substituted pyrrole derivatives are the compounds having the structure of Formula I,

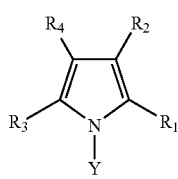

Formula I pharmaceutically acceptable salts, pharmaceutically acceptable solvates, prodrugs, metabolites, polymorphs, tautomers, racemates, pure enantiomers, diastereoisomers or N-oxides thereof, wherein:

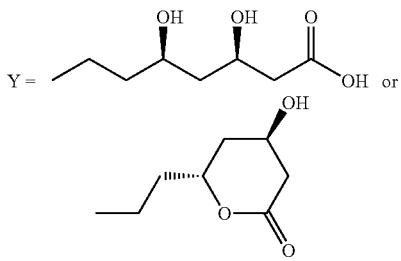

$R_1$ can be $C_1$-$C_6$, $C_3$-$C_6$, or optionally substituted phenyl (wherein up to three substituents are independently selected from halogens, $C_1$-$C_6$ alkyl, cyano, or $C_1$-$C_3$ perfluoroalkyl);
$R_2$ can be optionally substituted phenyl (wherein up to three substituents are independently selected from cyano, acetyl, or optionally substituted amino, wherein up to two amino substituents are independently selected from $C_1$-$C_6$ alkyl, $C_3$-$C_6$ cycloalkyl, acetyl, or sulfonamide);
$R_3$ can be optionally substituted $C_1$-$C_6$ alkyl or $C_3$-$C_6$ cycloalkyl (wherein substituents are independently selected from halogens, hydroxyl, $C_1$-$C_3$ alkoxy and protected hydroxyl);
$R_3$ can also be —$NR_8R_9$, wherein $R_8$ and $R_9$ are optionally substituted $C_1$-$C_6$ alkyl (wherein the optional substituent(s) is/are selected from halogens, hydroxy, $C_1$-$C_3$ alkoxy and protected hydroxyl);
$R_4$ can be

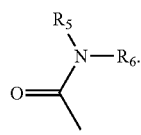

wherein $R_5$ and $R_6$ are independently hydrogen, $C_1$-$C_6$ alkyl or $C_3$-$C_6$ cycloalkyl, optionally substituted aryl or aralkyl, wherein the substituents are selected from halogens, cyano, optionally substituted $C_1$-$C_6$ alkyl (wherein up to two substituents are independently selected from hydroxyl, protected hydroxyl, and halogen(s)), optionally substituted amino (wherein up to two substituents are independently selected from $SO_2R_7$, $COR_7$, or $CONHR_7$, wherein $R_7$ is $C_1$-$C_6$ alkyl or aryl), or acetyl, trifluoromethyl, or $C_1$-$C_6$ alkoxycarbonyl, or $R_5$ and $R_6$ together form a 5-7 membered ring with one or more optional heteroatoms wherein the hetero atom(s) are independently selected from nitrogen, oxygen and sulfur,
or $R_4$ can be an optionally substituted mono-, bi- or tricyclic heterocycle having one or more hetero atom(s) wherein said hereto atom(s) is/are independently selected from oxygen, nitrogen and sulfur, and the optional substituents are independently selected from halogens, hydroxy, protected hydroxyl, $C_1$-$C_3$ alkoxy, cyano, $C_1$-$C_3$ perfluoroalkyl, $C_1$-$C_6$ alkyl or $C_3$-$C_6$ cycloalkyl, aryl or optionally substituted aralkyl wherein the substituents are independently selected from halogens, hydroxy, protected hydroxyl, $C_1$-$C_3$ alkoxy, cyano, or $C_1$-$C_3$ perfluoroalkyl, and the pharmaceutically acceptable salts, tautomers, racemates, pure enantiomers or diastereoisomers, and solvates of the compounds of Formula I, with the proviso that $R_2$ is phenyl only when (1) $R_5$ or $R_6$ is $C_3$-$C_6$ cycloalkyl or phenyl substituted with acetyl, alkyl, cycloalkyl, hydroxyalkyl, alkylsulfonamido, acetamido or (2) when $R_5$ and $R_6$ together form a 5-7 membered ring with or without one or more heteroatoms wherein the hetero atom(s) are selected from nitrogen, oxygen and sulfur or (3) when $R_5$ or $R_6$ is aralkyl optionally substituted with halogens, cyano, $C_1$-$C_6$ alkyl, $C_1$-$C_6$ halogenated alkyl or (4) when $R_4$ is optionally substituted mono-, bi- or tricyclic heterocycle having one or more hetero atom(s) (wherein the optional substituents are independently selected from halogens, hydroxy, protected hydroxyl, $C_1$-$C_3$ alkoxy, cyano, perfluoroalkyl of one to three carbon atoms, $C_1$-$C_6$ alkyl, $C_3$-$C_6$ cycloalkyl, aryl, or optionally substituted aralkyl (wherein the aralkyl substituents are independently selected from halogens, hydroxy, protected hydroxyl, $C_1$-$C_3$ alkoxy, cyano, or $C_1$-$C_3$ perfluoroalkyl).

Compounds of Formula I have shown utility in inhibiting 3-hydroxy-3-methylglutaryl-coenzyme A (HMG-CoA), among the key rate limiting steps in the biosynthetic pathway of cholesterol formation. These compounds hold promise for the treatment of cardiovascular diseases, for example, hypercholesterolemia or hyperlipidemia.

Compounds of Formula I have been described in PCT Publication No. WO 04/106299, which is incorporated herein by reference in its entirety. Substituted pyrrole derivatives as described herein may have the following attributes:
 (a) compounds ranging from being equipotent to 4-fold more potent than atorvastatin;
 (b) compounds being more potent than atorvastatin in inhibiting cholesterol synthesis in an in vivo rat model;
 (c) compounds having intrinsic clearance in human liver microsome significantly less than atorvastatin and not acting as a major substrate for CYP3A4 (cytochrome p450 3A4); and
 (d) compounds exhibiting potency and selectivity greater than atorvastatin in inhibition of cholesterol synthesis in rat primary hepatocytes over inhibition of cholesterol synthesis in extra hepatic cells/cell lines [e.g. NRK-49F (Fibroblast) and L6 (Myoblast)].

Particular illustrative compounds of the present invention for use in the combination products or medicaments, pharmaceutical compositions, pharmaceutical packages, pharmaceutical kits include:
(3R,5R)-7-[2-(4-fluorophenyl)-5-isopropyl-3-phenyl-4-[(2-acetylphenylamino) carbonyl]-pyrrol-1-yl]-3,5-dihydroxy-heptanoic acid,
(3R,5R)-7-[2-(4-fluorophenyl)-5-isopropyl-3-phenyl-4-[(3-acetylphenylamino) carbonyl]-pyrrol-1-yl]-3,5-dihydroxy-heptanoic acid, (3R,5R)-7-[2-(4-fluorophenyl)-5-isopropyl-3-phenyl-4-[(4-acetylphenylamino) carbonyl]-pyrrol-1-yl]-3,5-dihydroxy-heptanoic acid,
(3R,5R)-7-[2-(4-fluorophenyl)-5-isopropyl-3-phenyl-4-[(2,4-dimethylphenylamino) carbonyl]-pyrrol-1-yl]-3,5-dihydroxy-heptanoic acid,
(3R,5R)-7-[2-(4-fluorophenyl)-5-isopropyl-3-phenyl-4-[(cyclohexylamino)carbonyl)]-pyrrol-1-yl]-3,5-dihydroxy-heptanoic acid,
(3R,5R)-7-[2-(4-fluorophenyl)-5-isopropyl-3-phenyl-4-[(4-trifluoromethylbenzylamino) carbonyl)]-pyrrol-1-yl]-3,5-dihydroxy-heptanoic acid,
(3R,5R)-7-[2-(4-fluorophenyl)-5-isopropyl-3-phenyl-4-(morpholine-4-carbonyl)-pyrrol-1-yl]-3,5-dihydroxy-heptanoic acid,
(3R,5R)-7-[2-(4-fluorophenyl)-5-isopropyl-3-phenyl-4-(piperidine-1-carbonyl)-pyrrol-1-yl]-3,5-dihydroxy-heptanoic acid,
(3R,5R)-7-[2-(4-fluorophenyl)-5-isopropyl-3-phenyl-4-[(4-hydroxymethylphenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-methanesulfonylaminophenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-acetylaminophenylamino) carbonyl]-pyrrol-1-yl]-3,5-dihydroxy-heptanoic acid,
(3R,5R)-7-[2-(4-fluorophenyl)-5-isopropyl-3-(4-cyanophenyl)-4-[(phenylamino) carbonyl)]-pyrrol-1-yl]-3,5-dihydroxy-heptanoic acid,
(3R,5R)-7-[2-(4-fluorophenyl)-5-isopropyl-3-phenyl-4-[4-carboxyphenyl)amino) carbonyl]-pyrrol-1-yl]-3,5-dihydroxy-heptanoic acid,
(3R,5R)-7-[2-(4-fluorophenyl)-5-isopropyl-3-phenyl-4-[4-acetoxymethylphenyl)amino) carbonyl]-pyrrol-1-yl]-3,5-dihydroxy-heptanoic acid,
(3R,5R)-7-[2-(4-fluorophenyl)-5-isopropyl-3-phenyl-4-[4-phenylthiocarbamoyl oxymethylphenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-propionyloxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-octylcarbamoyloxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-phenylacetoxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-phenylcarbamoyl oxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-benzoyloxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-isonicotinoyloxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-pyridin-4-ylcarbamoyl oxymethyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-phenylcarbamoyl phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-cyclohexylcarbamoyl-phenyl)amino) carbonyl]-pyrrol-1-yl]-3,5-dihydroxy-heptanoic acid,
(3R,5R)-7-[2-(4-fluorophenyl)-5-isopropyl-3-phenyl-4-[4-methylcarbamoyl)-phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-benzylcarbamoyl)-phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-(morpholine-4-carbonyl)-phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-(piperidine-1-carbonyl)-phenyl)amino)carbonyl]-pyrrol-1-yl]-3,5-dihydroxy-heptanoic acid,
(3R,5R)-7-[2-(4-fluorophenyl)-5-isopropyl-3-phenyl-4-[4-benzylamino phenyl)amino) carbonyl]-pyrrol-1-yl]-3,5-dihydroxy-heptanoic acid,
(3R,5R)-7-[2-(4-fluorophenyl)-5-isopropyl-3-phenyl-4-[4-(1-hydroxyethyl)phenylamino) carbonyl]-pyrrol-1-yl]-3,5-dihydroxy-heptanoic acid,
(3R,5R)-7-[2-(4-fluorophenyl)-5-isopropyl-3-phenyl-4-[4-(2-hydroxyethyl)phenylamino) carbonyl]-pyrrol-1-yl]-3,5-dihydroxy-heptanoic acid,
(3R,5R)-7-[2-(4-fluorophenyl)-5-isopropyl-3-phenyl-4-[4-(3-hydroxypropyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-methoxymethyl phenylamino) carbonyl]-pyrrol-1-yl]-3,5-dihydroxy-heptanoic acid,
(3R,5R)-7-[2-(4-fluorophenyl)-5-isopropyl-3-phenyl-4-[(4-ethoxymethyl phenylamino) carbonyl]-pyrrol-1-yl]-3,5-dihydroxy-heptanoic acid,
(3R,5R)-7-[2-(4-fluorophenyl)-5-isopropyl-3-phenyl-4-[(4-isopropoxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-propoxymethyl phenylamino) carbonyl]-pyrrol-1-yl]-3,5-dihydroxy-heptanoic acid,
(3R,5R)-7-[2-(4-fluorophenyl)-5-isopropyl-3-phenyl-4-[(4-methoxymethoxymethylphenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-cyclohexyloxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-cyclopentyloxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-benzyloxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-chlorobenzyloxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-methoxybenzyloxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-phenoxymethylphenylamino) carbonyl]-pyrrol-1-yl]-3,5-dihydroxy-heptanoic acid,
(3R,5R)-7-[2-(4-fluorophenyl)-5-isopropyl-3-phenyl-4-[(4-chlorophenoxymethyl phenylamino)carbonyl]-pyrrol-1-yl]-3,5-dihydroxy-heptanoic acid,
(3R,5R)-7-[2-(4-fluorophenyl)-5-isopropyl-3-phenyl-4-[(4-acetylaminophenylamino) carbonyl]-pyrrol-1-yl]-3,5-dihydroxy-heptanoic acid,
(3R,5R)-7-[2-(4-fluorophenyl)-5-isopropyl-3-phenyl-4-[(4-benzoylamino phenylamino) carbonyl]-pyrrol-1-yl]-3,5-dihydroxy-heptanoic acid, (3R,5R)-7-[2-(4-fluorophenyl)-5-isopropyl-3-phenyl-4-[(4-benzenesulfonylamino phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-phenyl-ureido)-phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-methyl-ureido)-phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-benzyl-ureido)-phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-benzyl-thioureido)-phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-phenyl-thioureido)-phenylamino)carbonyl]-pyrrol-1-yl]-3,5-dihydroxy-heptanoic acid, (3R,5R)-7-[2-(4-fluorophenyl)-5-isopropyl-3-phenyl-4-[4-(3-methyl-thioureido)-phenylamino)carbonyl]-pyrrol-1-yl]-3,5-dihydroxy-heptanoic acid, pharmaceutically acceptable salts, pharmaceutically acceptable solvates, prodrugs, metabolites, polymorphs, tautomers, racemates, pure enantiomers, diastereoisomers or N-oxides thereof. In particular, pharmaceutically acceptable salts include hemi-calcium salts.

Dyslipidemic agents described herein can be selected from, but are not limited to: cholesteryl ester transfer protein (CETP) inhibitors, fibric acid derivatives/fibrates, antihypertensive agents, bile acid sequestrants, Acyl CoA-cholesterol acyltransferase inhibitors, cholesterol absorption inhibitors or other dyslipidemic agents.

Antiobesity agents described herein can be selected from, but are not limited to, 5-HT reuptake inhibitors, pancreatic lipase inhibitors, cannabinoid antagonists or recombinant human ciliary neurotropic factors.

Antihyperglycaemic agents described herein can be selected from, but are not limited to, insulin sensitizing agents/PPAR agonists, sulphonyl ureas, alpha glucosidase inhibitors, DPP4 inhibitors, GLP-1 analogs or agonists or other antihyperglycaemic agents.

Anti-inflammatory agents described herein can be selected from, but are not limited to, β2 agonists, COX-2 inhibitors, 5-lipooxygenase inhibitors, phosphodiesterase IV inhibitors, MMP inhibitors, TNF-α inhibitors, caspase inhibitors, p38 map kinase inhibitors, VLA-4 antagonists and PAF antagonists.

Dyslipidemic agents such as cholesteryl ester transfer protein (CETP) inhibitors, fibric acid derivatives/fibrates, antihypertensive agents, bile acid sequestrants, acyl CoA-cholesterol acyltransferase (ACAT) inhibitors or cholesterol absorption inhibitors; antiobesity agents such as 5-HT reuptake inhibitors, pancreatic lipase inhibitors, cannabinoid antagonists or recombinant human ciliary neurotropic factors; antihyperglycaemic agents such as insulin sensitizing agents/PPAR agonists, sulphonyl ureas, biguanides, alpha glucosidase inhibitors, DPP4 inhibitors or GLP-1 analogs or agonists; anti-inflammatory agents such as β2 agonists, COX-2 inhibitors, 5-lipooxygenase inhibitors, phosphodiesterase IV inhibitors, MMP inhibitors, TNF-α inhibitors, caspase inhibitors, p38 map kinase inhibitors, VLA-4 antagonists or PAF antagonists may be widely chosen from among those known in the prior art or subsequently discovered and/or hereafter discovered and/or hereafter developed.

CETP inhibitors can be selected, for example, from those compounds described in U.S. Pat. Nos. 6,803,388; 6,787,570; 6,586,448; 6,489,478; 6,395,751; 6,197,786; 6,147,090; 6,753,346; 6,426,365 and 6,794,396; European Patent Nos. 0818448 and 0818197. Examples of CETP inhibitors include, but are not limited to, torcetrapib, JTT-705 or CP 532623, for example.

Fibric acid derivatives or fibrates can be selected, for example, from compounds described in U.S. Pat. Nos. 4,051,143; 3,723,446; 4,058,552; 3,674,836; 3,781,328; 3,948,943; 3,716,583 and 3,984,413. Examples of fibric acid derivatives or fibrates include, but are not limited to, etofibrate, fenofibrate, clofibrate, gemfibrozil, bezafibrate, ciprofibrate, clinofibrate or theofibrate, for example.

Antihypertensive agents can be selected from calcium channel blocker, ACE inhibitors, angiotensin II receptor antagonists, beta-adrenergic receptor blockers, alpha-adrenergic receptor antagonists or diuretics.

Calcium channel blockers can be selected, for example, from compounds described in U.S. Pat. Nos. 4,663,325; 3,932,645; 4,154,839; 3,773,939; 4,466,972; 4,801,599; 4,705,797; 4,994,461; 4,572,909; 4,879,303; 5,155,120; 3,962,238; 3,562,257; 3,262,977; 4,448,964; 4,672,068 and 4,264,611. Examples of calcium channel blockers include, but are not limited to, amlodipine, its salts and prodrugs thereof, lomerizine, isradipine, lacidipine, lercadipine, manidipine, benidipine, cilnidipine, felodipine, bepridil, diltiazem, fendiline, nicardipine, nimodipine, nilvadipine, nitrendipine, nisoldipine, zonisamide or nifedipine, their salts and prodrugs thereof, for example.

Angiotensin converting enzyme inhibitors (ACE inhibitors) can be selected, for example, from compounds described in U.S. Pat. Nos. 4,472,380; 4,337,201; 4,508,729; 4,425,355; 4,699,905; 4,470,972; 4,344,949; 4,587,258; 4,822,818; 4,410,520; 4,248,883 and 4,105,776. Examples of angiotensin converting enzyme inhibitors include, but are not limited to, fosinopril, lisinopril, ramipril, temocapril, trandolapril, spirapril, quinapril, perindipril, enalapril, delapril, captopril, alacepril or benzapril, for example.

Angiotensin II receptor antagonists can be selected, for example, from compounds described in U.S. Pat. Nos. 5,399,578; 5,185,351; 5,128,355 and 5,559,233. Examples of angiotensin II receptor antagonists include, but are not limited to, telmisartan, valsartan, eprosartan, irbesartan or losartan, for example.

Beta-adrenergic receptor blockers can be selected, for example, from compounds described in U.S. Pat. Nos. 3,857,952; 4,217,305; 3,932,400; 3,471,515; 3,341,584; 4,032,648; 4,129,565; 3,655,663; 3,483,221; 3,982,021; 3,998,790; 3,649,691; 3,910,924; 4,503,067; 4,034,009; 4,310,549; 4,012,444; 4,252,825; 3,868,460; 3,663,570; 4,434,176; 4,258,062; 3,934,032; 4,056,626; 4,252,984 and 3,857,891. Examples of beta-adrenergic receptor blockers include, but are not limited to, acebutolol, amosulol, arotinolol, atenolol, befunolol, betaxolol, bevantolol, bisprolol, bopindolol, bucumolol, bunitrolol, butofilolol, carteolol, carvedilol, celiprolol, cloranolol, labetalol, levobunolol, mepindolol, metoprolol, nadolol, oxprenolol, pindolol, satalol, tertatolol, tilisolol and timolol, for example.

Alpha-adrenergic receptor antagonists can be selected, for example, from compounds described in U.S. Pat. Nos. 3,669,968; 4,731,478; 3,527,761; 3,997,666; 3,879,554; 3,663,706; 4,188,390; 4,252,721; 3,932,400 and 4,217,305. Examples of alpha-adrenergic receptor antagonists include, but are not limited to, amosulol, arotinolol, dapiprazole, doxazosin, indoramin, naftopidil, nicergoline, prazosin, tamsulosin and trimazosin, for example.

Bile acid sequestrants can be selected, for example, from compounds described in U.S. Pat. Nos. 5,693,675 and 3,576,883. Examples of bile acid sequestrants include, but are not limited to, cholestyramine, colestipol, covesevelam, probucol or nicotinic acid, for example.

Acyl CoA-cholesterol acyltransferase inhibitors (ACAT inhibitors) can be selected, for example, from compounds described in U.S. Pat. Nos. 5,491,172, 5,990,173; 5,733,931; U.S. Application No. 2005/017, and PCT Publication No. WO 2003077896. Examples of acyl CoA-cholesterol acyltransferase inhibitors include, but are not limited to, F-12511 or NTE-122, for example.

Cholesterol absorption inhibitors can be selected, for example, from compounds described in U.S. Pat. No. 5,767,115. Examples of cholesterol absorption inhibitors include, but are not limited to, ezetimibe, for example.

Other dyslipidemic agents that can be used comprises of bile acid reabsorption inhibitors, triglyceride synthesis inhibitors, MTP inhibitors, transcription modulators, squalene epoxidase inhibitors, LDL receptor inducers, platelet aggregation inhibitors, fish oils, omega 3 fatty acids, farnesoid X receptor agonists, liver X receptors, squalene synthase inhibitors, microsomal triglyceride or guggul lipids, for example.

5-HT reuptake inhibitors can be selected, for example, from compounds disclosed in U.S. Pat. Nos. 4,314,081; 3,912,743; 5,985,322; 5,744,501 and 4,522,828. Examples of 5-HT reuptake inhibitors include, but are not limited to, fluoxetine, femoxetine, fluoxetine, sertraline or sibutramine, for example.

Pancreatic lipase inhibitors can be selected, for example, from compounds described in U.S. Pat. No. 4,598,089. Examples of pancreatic lipase inhibitors include, but are not limited to, orlistat, for example.

Cannabinoid antagonists can be selected, for example, from compounds described in U.S. Pat. No. 5,624,941. Examples of cannabinoid antagonists include, but are not limited to, rimonabant, for example.

Recombinant human ciliary neuroleptic factors can be selected, for example, from agents described in U.S. Pat. No. 5,349,056. Examples of recombinant human ciliary neuroleptic factors include, but are not limited to, axokine, for example.

Insulin sensitizing agents/PPAR agonists can be selected, for example, from compounds described in U.S. Pat. No. 3,454,635; 4,444,779; 4,687,777; 5,002,953; 5,968,982 or 4,701,559; U.S. Application Nos. 60/528/303; 60/530,334; 60/562,085; 60/562,009; and Indian Patent Application No. 1109/DEL/2005. Examples of insulin sensitizing agents/PPAR agonists include, but are not limited to, pioglitazone, rosiglitazone, or dual agonists (e.g., muraglitazar), for example.

Sulphonyl ureas can be selected, for example, from compounds described in U.S. Pat. No. 3,454,635. Examples of sulphonyl ureas include, but are not limited to, glibenclamide. Biguanides can be, for example, metformin, for example.

Alpha glucosidase inhibitors can be selected, for example, from compounds described in U.S. Pat. Nos. 4,062,950; 4,260,622; 4,182,767; 4,701,559; and PCT Publication No. WO 04/039373. Examples of alpha glucosidase inhibitors include, but are not limited to, acarbose, miglitol, miglustat or voglibose, for example.

Dipeptidyl-peptidase IV (DPP-IV) inhibitors can be selected, for example, from compounds described in PCT Publication No. 98/19998. Examples of DPP4 inhibitors include, but are not limited to, acarbose, miglitol, miglustat or voglibose, for example.

Glucagon-like peptide I agonists can be selected, for example, from agents described in U.S. Pat. Nos. 5,424,286, and 6,329,336. Examples of glucagon-like peptide I agonists include, but are not limited to, exendin-4, liraglutide or CJC-1131, for example.

$\beta$2-agonists can be selected, for example, from compounds described in U.S. Pat. Nos. 3,705,233; 3,644,353; 3,642,896; 3,994,974; 3,937,838 and 4,011,258. Examples of $\beta$2-agonists include, but are not limited to, albuterol, formoterol, terbutaline or metaproterenol, for example.

COX-2 inhibitors can be selected, for example, from compounds described in U.S. Pat. Nos. 5,932,598; 5,633,272; 5,474,995 and 5,466,823. The disclosures of these patents are incorporated herein by reference in their entireties. Examples of COX-2 inhibitors include, but are not limited to, parecoxib, valdecoxib or rofecoxib, for example.

5-lipooxygenase inhibitors can be selected, for example, from compounds described in U.S. Pat. No. 4,873,259, European Patent Nos. 419049, 542356 and 542355. Examples of 5-lipooxygenase inhibitors include, but are not limited to, zileuton or atreluton, for example.

Phosphodiesterase IV inhibitors can be selected, for example, from compounds described in PCT Publication Nos. WO 05/021515, WO 05/051931, Co-pending Indian patent application No. 303/DEL/2005, U.S. Pat. Nos. 5,552,438; 5,712,298; U.S. Application Nos. 60/525,347; 60/498,947; and 60/529,824. The disclosures of these publications are incorporated herein by reference in their entireties. Examples of phosphodiesterase IV inhibitors include, but are not limited to, RBx-11082, cilomilast or roflumilast.

MMP inhibitors can be selected, for example, from the compounds described in European Patent Nos. 651739 and 606646, and U.S. Pat. No. 5,753,653. The disclosures of these publications are incorporated herein by reference in their entireties. Examples of MMP inhibitors include, but are not limited to, batimastat (BB-94), marimastat (BB-2516), prinomastat (AG3340), BAY 12-9566 or CGS27023A.

TNF-$\alpha$ inhibitors can be selected, for example, from the compounds disclosed in U.S. Pat. Nos. 5,344,915; 6,015,557 and 5,994,510. The disclosures of these publications are incorporated herein by reference in their entireties. Examples of TNF-$\alpha$ inhibitors include, but are not limited to, infliximab, etanercept, D2E7 or CDP 571.

Caspase inhibitors can be selected, for example, from compounds described in PCT Publication No. WO 97/22619. Examples of caspase inhibitors include, but are not limited to, pralnacasan (Vx-740), for example.

p38 Map Kinase inhibitors can be selected, for example, from compounds described in PCT Publication Nos. Examples of p38 Map Kinase inhibitors include, but are not limited to, Vx-745, BIRB-796, RWJ-67657 or SB-239063, for example.

VLA-4 antagonists are selected, for example, from compounds described in U.S. Pat. Nos. 6,329,344; 6,590,085 and 5,510,332; PCT Publication Nos. WO00/18759, WO00/18760, WO00/15612, WO00/05224, WO05/026163, WO00/05223, WO 00/01690, WO 00/00477, WO 99/67230, WO 99/61465, WO 99/54321, WO 99/47547, WO 99/43642, WO 99/37618, WO 99/37605, WO 99/36393, WO 99/35163, WO 99/24398, WO 99/23063, WO 98/58902, WO 98/54207, WO 97/03094, WO 97/02289, WO 96/40781, WO 96/40641, WO 96/31206, WO 96/22966, WO 96/20216, WO 96/06108, WO 96/01644, WO 95/15973, WO 98/53818, WO 98/53814 and WO 98/53817; European Publication Nos. 0918059, 0842943, 0905139 and 0903353. Examples of VLA-4 antagonists include, but are not limited to, clafrinast or RBx-7796, for example.

Platelet-activating factor (PAF) antagonists can be selected, for example, from compounds described in U.S. Pat.

Nos. 5,155,103; 3,850,941; 5,274,094; 5,422,351; 5,541,183; 5,049,559; 4,734,280 and 5,492,906. Examples of PAF antagonists include, but are not limited to, apafant, ibudilast, lexipafant, rupatadine or ginkgolides (e.g. ginkgolide A, B or C) and derivatives thereof, for example.

Aspects of this invention include the following. For example, combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one CETP inhibitor. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, torcetrapib, JTT-705 or CP 532623.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one fibric acid derivative/fibrate. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, etofibrate, fenofibrate, clofibrate, gemfibrozil, bezafibrate, ciprofibrate, clinofibrate or theofibrate.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, at least one antihypertensive agent. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, amlodipine, lomerizine, isradipine, lacidipine, lercadipine, manidipine, benidipine, cilnidipine, felodipine, bepridil, diltiazem, fendiline, nicardipine, nimodipine, nilvadipine, nitrendipine, nisoldipine or nifedipine.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and fosinopril, lisinopril, ramipril, temocapril, trandolapril, spirapril, quinapril, perindipril, enalapril, delapril, captopril, alacepril or benzapril. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, valsartan, eprosartan, irbesartan or losartan.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, acebutolol, amosulol, arotinolol, atenolol, befunolol, betaxolol, bevantolol, bisprolol, bopindolol, bucumolol, bunitrolol, butofilolol, carteolol, carvedilol, celiprolol, cloranolol, labetalol, levobunolol, mepindolol, metoprolol, nadolol, oxprenolol, pindolol, satalol, tertatolol, tilisolol or timolol.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, amosulol, arotinolol, dapiprazole, doxazosin, indoramin, naftopidil, nicergoline, prazosin, tamsulosin or trimazosin.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one bile acid sequestrant. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, cholestyramine, colestipol, covesevelam, probucol or nicotinic acid.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one acyl CoA-cholesterol acyltransferase inhibitor (ACAT inhibitors). The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example, F-12511 or NTE-122.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one cholesterol absorption inhibitor. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example ezetimibe.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and at least one antihyperglycaemic agent, for example, insulin sensitizing agents/PPAR agonists, sulphonyl ureas, biguanides, alpha glucosidase inhibitors, DPP IV inhibitors GLP-1 agonists or mixtures thereof. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example metformin, pioglitazone, rosiglitazone, glibenclamide, acarbose, miglitol, miglustat, voglibose, NVP-728, vildagliptin, exendin-4, liraglutide, albugon, CJC-1131 or mixtures thereof.

The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and, for example one or more 5-HT reuptake inhibitors, pancreatic lipase inhibitors, cannabinoid antagonists, recombinant human ciliary neuroleptic factors, β2-agonists, COX-2 inhibitors, 5-lipooxygenase inhibitors, phosphodiesterase IV inhibitors, MMP inhibitors, TNF-α inhibitors, caspase inhibitors, p38 Map Kinase inhibitors, VLA-4 antagonists, PAF antagonists or mixtures thereof. The combination products or medicaments, pharmaceutical compositions, pharmaceutical packages, pharmaceutical kits and methods for treating cardiovascular diseases, Alzheimer's disease, obesity, diabetes or inflammatory diseases involve a therapeutically effective amount of at least one substituted pyrrole derivative of Formula I and fluoxetine, femoxetine, fluoxetine, sertraline, sibutramine, orlistat, rimonabant, axokine, albuterol, formoterol, terbutaline, metaproterenol, parecoxib, valdecoxib, rofecoxib, zileuton, atreluton, cilomilast, roflumilast, batimastat (BB-94), marimastat (BB-2516), prinomastat (AG3340), BAY 12-9566, CGS 27023A, infliximab, etanercept, D2E7, CDP 571, pralnacasan (Vx-740), Vx-745, BIRB-796, RWJ-67657, SB-239063, clafrinast, apafant, ibudilast, lexipafant, rupatadine, ginkgolides (e.g. ginkgolide A, B or C and derivatives thereof) or mixtures thereof.

The term "cardiovascular disease" as used herein refers to any disorder in any of the various parts of cardiovascular system, which is made up of heart and blood vessels throughout the body. The combination pharmaceutical compositions disclosed herein are intended to be used for the treatment or prophylaxis of disease or disorder of heart (cardio) and the disease or disorder of blood vessels (vascular). Some examples of cardiovascular disease include, but are not limited to, arteriosclerosis, atherosclerosis, hypercholesterolemia, hyperlipidemia, hyperlipoproteinemia, hypertriglyceridemia, hypertension, stroke, ischemia, peripheral vascular disease, peripheral arterial disease, coronary heart disease, myocardial infarction, cerebral infraction, myocardial microvascular disease, osteoporosis, osteopenia, angina, resterosis or diabetes and related disorders.

The term "inflammatory disease" as used herein refers to any disease, condition, trait, genotype or phenotype characterized by an inflammatory or allergic process as is known in the art such as inflammation, acute inflammation, chronic inflammation, respiratory disease, atherosclerosis, restenosis, asthma, COPD, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses, and any other inflammatory disease, condition, trait, genotype or phenotype that can respond to the modulation of disease related gene expression in a cell or tissue, alone or in combination with other therapies.

The term "pharmaceutical package" as used herein refers to any package useful for stable storage of the dosage form, comprising (a) single pharmaceutical composition comprising a therapeutically effective amount of at least one substituted pyrrole derivative, at least one dyslipidemic agent, antiobesity, or antihyperglycaemic agent, anti-inflammatory agent or mixtures thereof, optionally together with pharmaceutically acceptable carriers, or (b) a first pharmaceutical composition comprising a therapeutically effective amount of at least one substituted pyrrole derivative, optionally together with a pharmaceutically acceptable carrier, a second pharmaceutical composition comprising at least one dyslipidemic agent, antiobesity, or antihyperglycaemic agent, anti-inflammatory agent or mixtures thereof, optionally together with pharmaceutically acceptable carriers. The package may, for example, be a glass, plastic, strip pack or blister pack.

The term "pharmaceutical kit" as used herein refers to a kit containing (a) a single pharmaceutical composition comprising a therapeutically effective amount of at least one substituted pyrrole derivative; one or more dyslipidemic agents, antiobesity, antihyperglycaemic agents, anti-inflammatory agents or mixtures thereof, optionally together with pharmaceutically acceptable carriers; prescribing information and a container, or (b) a first pharmaceutical composition comprising a therapeutically effective amount of at least one substituted pyrrole derivative, optionally together with pharmaceutically acceptable carriers, a second pharmaceutical composition comprising one or more dyslipidemic agents, antiobesity, antihyperglycaemic agents, anti-inflammatory agents or mixtures thereof, optionally together with pharmaceutically acceptable carriers; prescribing information and a container. The prescribing information, for example, may include pharmacodynamics, pharmacokinetics, indications and usages, direction of administration, warnings, dosage or adverse effects of each pharmaceutical. The container in the kit provides means for separating the first and second pharmaceutical compositions. The container may, for example, be a divided bottle or divided foil packet, for example, blister pack.

The term "combination pharmaceutical composition" as used herein refers to, in one embodiment; a single pharmaceutical composition comprising at least one substituted pyrrole derivative and one or more dyslipidemic agents, antiobesity, antihyperglycaemic agents, anti-inflammatory agents or mixtures thereof, optionally together with pharmaceutically acceptable carriers. The combination pharmaceutical composition, in a second embodiment, refers to a first pharmaceutical composition comprising therapeutically effective amount of at least one substituted pyrrole derivatives, optionally together with pharmaceutically acceptable carriers, a second pharmaceutical composition comprising one or more dyslipidemic agents, antiobesity, antihyperglycaemic agents, anti-inflammatory agents or mixture thereof, optionally together with pharmaceutically acceptable carriers. The separate pharmaceutical composition can be administered simultaneously, separately or sequentially.

Included within the scope of this invention are pharmaceutically acceptable salts of compounds of Formula I. The pharmaceutically acceptable salts include, for example, alkali metal (e.g., sodium or potassium) or alkaline earth metal (e.g., calcium or magnesium) salts and addition salts of acids or bases. Suitable pharmaceutically acceptable acid addition salts may be prepared from an inorganic acid or from an organic acid. Example of such inorganic acids include, but are not limited to, hydrochloric, hydrobromic, hydroiodic, sulfuric, phosphoric acid and like. Appropriate organic acids include, but not limited to, aliphatic, cycloaliphatic, aromatic, heterocyclic, carboxylic and sulfonic classes of organic acids, such as, formic, acetic, propionic, succinic, glycolic, gluconic, lactic, malic, tartaric, dihydroxytartaric acid, citric, ascorbic, glucuronic, maleic, fumeric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, beta-hydroxybutyric, cyclohexylaminosulfonic, galactaric and galacturonic acid and the like.

Pharmaceutically acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, and procaine and the like.

The present invention also includes within its scope prodrugs of the agents disclosed herein. In general, such prodrugs will be functional derivatives of these compounds, which are readily convertible in vivo into the required compound. Conventional procedure for the selection and preparation of suitable prodrug derivatives are described, for example, in "Design of Prodrugs", Bundgaard, Elsevier, 1985. The present invention also includes metabolites, which become active upon introduction into the biological system. Where the compounds have at least one chiral center, they may accordingly exist as enantiomers. Where the compounds according to invention possess two or more chiral centers, they may additionally exist as diastereomers. All such individual isomers and racemates therefore are encompassed within the scope of the present invention. Furthermore, some of the crystalline forms for compounds described herein may exist as polymorphs and are included in the present invention. In addition, some of the compounds described herein may form solvates with water (i.e., hydrates) or common organic solvents. Such solvates are also encompassed within the scope of this invention.

The single composition containing at least one substituted pyrrole derivative and one or more dyslipidemic agents, antiobesity, or antihyperglycaemic agents, anti-inflammatory agents or mixtures thereof, or separate compositions of at least one substituted pyrrole derivative and one or more dyslipidemic agents, antiobesity, or antihyperglycaemic agents, anti-inflammatory agents or mixtures thereof may be suitable for oral, parenteral, topical, transdermal administration. The composition may be formulated to provide immediate or sustained release of the therapeutic agents. The agents described herein can be administered alone but will generally be administered as an admixture with a suitable "pharmaceutically acceptable carrier". The term "pharmaceutically acceptable carrier" is intended to include non-toxic, inert solid, semi-solid or liquid filter, diluent, encapsulating material or formulation auxiliary of any type.

Solid form preparations for oral administration may include capsules, tablets, pills, powder, granules and suppositories. For solid form preparation, the active compound can be mixed with at least one inert, pharmaceutically acceptable excipient or carrier such as sodium citrate, dicalcium phosphate and/or a filter an extender such as starch, lactose, sucrose, glucose, mannitol and silicic acid; binders such as carboxymethyl cellulose, alginates, gelatins, polyvinylpyrrolidinone, sucrose, acacia; disintegrating agents such as agar-agar, calcium carbonate, potato starch, aliginic acid, certain silicates and sodium carbonate; absorption accelerators such as quaternary ammonium compounds; wetting agents such as cetyl alcohol, glycerol, monostearate; adsorbents such as kaolin; lubricants such as talc, calcium stearate, magnesium stearate, solid polyethyleneglycol, sodium lauryl sulphate and mixtures thereof.

In case of capsules, tablets, pills, the dosage form may also comprise buffering agents. The solid preparation of tablets, capsules, pills, granules can be prepared with coating and shells such as enteric coating and other coatings well known in the pharmaceutical formulating art.

Liquid form preparation for oral administration includes pharmaceutically acceptable emulsions, solution, suspensions, syrups and elixirs. For liquid form preparation active compound is mixed with water or other solvent, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (such as cottonseed, groundnut, corn, germ, olive, castor and sesame oil), glycerol and fatty acid ester of sorbitan and mixtures thereof.

Besides inert diluents, the oral composition can also include adjuvants such as wetting agents, emulsifying agents, suspending agents, sweetening agents, flavoring agents and perfuming agent.

Injectable preparations such as sterile injections, aqueous or oleaginous suspensions may be formulated according to the art using suitable dispersing or wetting and suspending agents. Among the acceptable vehicles and solvents that may be employed are water, Ringer's solution and isotonic sodium chloride.

Dosage form for topical or transdermal administration includes ointments, pastes, creams, lotions, gel, powders, solutions, spray, inhalants or patches. The active compound is admixed under sterile condition with a pharmaceutically acceptable carrier and any needed preservatives or buffer as may be required.

The pharmaceutical preparation is in unit dosage form. In such form, the preparation is subdivided into unit doses containing appropriate quantities of the active component.

The formulation as described herein may be formulated so as to provide quick sustained, or delayed release of the active ingredient after administration to the patient by employing procedure well known to the art. The composition may be administered as a depot formulation that permits sustained release, limits access to general circulation. Such a formulation may be provided as a slow release implant, be microencapsulated, or attached to a biodegradable polymer. The compound is administered in a sustained release formulation as a tablet or capsule. A sustained release formulation is a preparation that releases the active component over a desired period of time after administration. A sustained release formulation is prepared by applying a biodegradable, bioerodible or bioabsorbable polymeric formulation that is compatible on the surface of the active component. Examples of sustained release formulation include, but are not limited to, hydroxypropylmethylcellulose (HPMC), hydrogenated vegetable oil (HVO), ethylcellulose, polyvinylpyrrolidione, pyran copolymer, polyhydroxypropylmethacryl-amidephenol, polyhydroxy-ethylaspartamidephenol, or polyethyleneoxidepolylysin substituted with palmitoyl residues, polylactic acid, polyepsilon caprolactone, polyhydroxy butyric acid, polyorthoesters, polyacetals, polydihydro-pyrans, or polycyano acrylates.

The term "biodegradable" means that the polymeric formulation degrades overtime by the action of enzymes, by hydrolytic action and/or by other similar mechanisms in the human body. By "bioerodible" it is meant that the polymeric formulation erodes or degrades over time due, at least in part, to contact with substances found in the surrounding tissue fluids or cellular action. By "bioabsorbable", it is meant that the polymeric formulation is broken down and absorbed within the body of a mammal, for example, by a cell or tissue. "biocompatible" means that the polymeric formulation does not cause substantial tissue irritation or necrosis.

The pharmaceutical compositions as described herein can be administered together combined in a single dosage form or they can be administered separately, simultaneously or sequentially, each in its dosage form but as part of the same therapeutic treatment program or regimen. Separate administration of each compound, at different times and by different routes, will sometimes be recommended.

The dosage forms disclosed herein can be prepared by conventional methods known to a person ordinary skilled in the art. The dosage of the pharmaceutical composition of the present invention may be appropriately determined with reference to the dosages recommended for the respective active components and can be selected according to the recipient, the age and body weight, current clinical status, administration time, dosage form, method of administration, and combination of the active components, among other factors.

The pharmaceutical composition of the present invention can show a marked synergistic effect compared with administration of either active component alone. Furthermore, since the pharmaceutical composition of the present invention develops sufficient efficacy with reduced doses as compared with the administration of any one of the active components alone, the side effects of the respective components can be reduced.

The following assays can be performed to show the utility of the combinations of the present invention. The following assays are illustrative and do not limit the scope of this invention. Other assay methods known in the art can also be used to show the utility of the combinations described herein.

EXAMPLE 1

Measurement of Hepatic Cholesterol and Triglyceride Concentration (I) Total lipids are extracted with an organic solvent mixture of hexane and isopropanol. Extracted lipids are emulsified by sonication in a buffer containing 1,4-piperazinediethanesulfonic acid, magnesium chloride.6H2O, free fatty acids-bovine serum albumin, and sodium dodecyl sulfate. Lipid concentrations from the resulting emulsion can then be assessed using commercial enzymatic kits. Reference: Rodriguez-Sureda et al., *Anal. Biochem.*, 343: 277-282 (2005).

(II) Triglyceride, free cholesterol, and total cholesterol are quantified in lipid extracts of liver from nonhuman primates using commercially available enzymatic reagents. Lipids are solubilized in water by the addition of Triton X-100. This method has the advantage of measuring each lipid class from a single sample preparation. Reference: Carr et al., *Clin. Biochem.*, 26: 39-42 (1993).

EXAMPLE 2

Measurement of Hepatic Enzymes (I) HMG-COA reductase activity: HMG-COA reductase activity is determined with slight modification of the protocol of Harwood et al. (1993). Rat liver microsomes are prepared. Microsomal aliquots in TEDK Buffer containing NADP, glucose-6-phosphate, glucose-6-phosphate dehydrogenase, [14C] HMG-CoA, [3H]mevalonate as an internal standard EDTA to prevent conversion of mevalonate to phosphomevalonate during incubation are incubated at 37° C. After incubation, HCl is added to terminate the enzymatic reaction and to convert the newly formed mevalonate into mevalonolactone. The mevalonolactone is then separated from unreacted substrate by ion-exchange chromatography and the radioactivity is counted by scintillation counter. Reference: Harwood et al., *J. Lipid Res.*, 34: 377-395 (1993).

(II) Measurement of hepatic cholesterol 7-alpha hydroxylase activity: Hepatic cholesterol 7α-hydroxylase (CYP7A1) is major regulatory enzyme in the synthesis of bile acids and its activity is determined according to the procedure of Shefer et al., (1981). Rat liver acetone powder which is depleted with endogenous cholesterol is used as the source of the enzyme and incubated with [4-$^{14}$C] cholesterol for 20 min. at 37° C. After the termination of the reaction, sterol fraction is extracted. The product, 7-beta-hydroxycholesterol is separated from the reactant by TLC and the radioactivity is counted by scintillation counter. Reference: Shefer et al., *J. Lipid Res.*, 22:532-536 (1981).

EXAMPLE 3

Determination of Serum Lipids (I) Total Cholesterol: Cholesterol esters in serum are hydrolysed by cholesterol esterase. The free cholesterol is then oxidized by cholesterol oxidase to the corresponding ketone liberating hydrogen peroxide, which is then converted to water and oxygen by the enzyme peroxidase. Para aminophenazone (4 aminophenazone) takes up the oxygen and together with phenol forms a pink coloured quinoneimine dye, which is measured at 515 nm/yellow green filter. Reference: Allain et al., *Clin. Chem.*, 20: 470 (1974).

Commercial kits: Cholesterol assay kit (Roche Molecular Biochemicals diagnostic kit & Ranbaxy diagnostics).

(II) HDL-C: The HDL-C assay is based on an immunoinhibition. Antihuman ⊕-lipoprotein antibody in Reagent 1 binds to lipoproteins (LDL, VLDL, chylomicrons) other than HDL. The antigen antibody complexes are formed, block enzyme reactions when reagent 2 is added. Hydrogen peroxide produced by the enzyme reacts with HDL-C to yield a blue color complex upon oxidase condensation with PDAOS and 4-aminoantipyrine in the presence of peroxidase (POD). By measurement of the blue color complex produced, the HDL-C concentration of the sample can be quantitated. This assay shows good correlation with the reference methods, no interference from coexisting substances, and is convenient with ready-to-use reagents. Stability and a high degree of linearity add to the benefits of this assay. Reference: Sampson et al., *Clin. Chem.*, 47 (3): 532-539 (2001).

Commercial kits: HDL-C Assay test kit (Wako). Triple Lipid Screening Test: A Homogeneous Sequential Assay for HDL-Cholesterol, Total Cholesterol, and Triglycerides.

(III) Triglyceride: Triglycerides are hydrolysed and free glycerol is then oxidized by oxidase to the corresponding ketone liberating hydrogen peroxide, which is then converted to water and oxygen by the enzyme peroxidase. Para aminophenazone (4 aminophenazone) takes up the oxygen and together with phenol forms a pink coloured quinoneimine dye, which can be measured at 545 nm/yellow green filter. Reference: Geary, *Med. J. Aust.*, 22 (1): 385-387 (1975).

Commercial kit: Triglyceride assai kit (Ranbaxy diagnostics, Wako & Sigma)

(IV) LDL-C: The method for estimating the cholesterol content of the serum low-density lipoprotein fraction involves measurements of fasting plasma total cholesterol, triglyceride, and high-density lipoprotein cholesterol concentrations. The concentration of LDL-C can be calculated using following equation, LDL-C=TC−HDL-C−TG/5. Reference: Friedewald et al, *Clin. Chem.,* 18, 6, (1972).

This method cannot be used if triglyceride is more than 400 mg/dl. In such case following kits can be used for direct estimation.

The Wako L-Type LDL-C assay is homogeneous, with ready-to-use reagents which eliminates the preparatory steps or calculation and can be applied to automated chemistry analyzers. The Wako L-Type LDL-C assay follows a two-step reaction which in the first step eliminates non-LDL cholesterol (Reagent 1) and in the second step a color reaction of the LDL cholesterol (Reagent 2). By measuring the blue color complex produced at 600 nm, the LDL-C of the sample is quantitated.

Commercial kits: LDL-C assays Kit (Wako & Genzyme Diagnostic)

(V) VLDL-C: The assay for estimating VLDL-C is based on immunoturbidimetry using monospecific goat anti-human serum. The turbidity is measured using Hitachi 912™ analyzer (Roche Diagnostics, Indianapolis, Ind., USA). Reference: Rifai et al., *Clin. Chem.,* 32 (6): 957-961 (1986).

An alternative approach to estimate VLDL-C is through a formula in which TG is first estimated and then VLDL-C is = 0.166×TG. This equation shows equal or improved accuracy with this estimation procedure, particularly at high TG levels. Reference: Wilson et al., *Clin. Chim. Acta.,* October 15; 1513):285-91 (1985).

(VI) NEFA: This NEFA assay utilizes an in vitro enzymatic calorimetric methodology, which eliminates the need for an extraction procedure and can be automated using your existing clinical chemistry instrumentation. This enzymatic method relies upon the acylation of coenzyme A(CoA) by the fatty acids in the presence of added acyl-CoA synthetase (ACS). The acyl-CoA produced is oxidized by added acyl-CoA oxidase (ACOD) with the generation of hydrogen peroxide. Hydrogen peroxide, in the presence of peroxidase (POD) permits the oxidative condensation of 3-methyl-N-ethyl-N-(b-hydroxyethyl)-aniline (MEHA) with 4-aminoantipyrine to form a purple color which is measured spectrophotometrically at 550 n.

Commercial kits: NEFA Assay test kit (Wako & Roche)

(VII) Serum/plasma lipid measurement: Serum/plasma lipid is measured spectrophotometrically using phospho.vanillin reagent. The linearity of the method is up to 1250 mg/dl. Concentrations up to 1240 mg/dl or of bilirubin up to 20 mg/dl in the serum do not interfere. Reference: Frings et al., *Clin. Chem.,* Vol. 18 (7): (1972).

EXAMPLE 4

Bile Acid Measurement

In the presence of Thio-NAD, the enzyme 3-á hydroxysteroid dehydrogenase (3-á HSD) converts bile acids to 3-keto steroids and Thio-NADH. In the presence of excess NADH, the enzyme cycling occurs efficiently and the rate of formation of Thio-NADH is determined by measuring specific change of absorbance at 405 nm. Reference: Textbook of Natural Medicine copyright: Pizzomo & Murray, 1987, 1992.

Commercial Kit: Total Bile Acid Enzyme Assay kit (Catalog No: BQ042A, Bio-Quant)

PPAR-α Transactivation Assay: Transactivation assays are performed using full length PPARα construct, rat PPAR response element (rat PPRE) in HEK-293 cell line as reported previously with slight modifications (Frederiksen et al., 2004).

Briefly, $1 \times 10^6$ cells are plated per well in a six-well plate. After overnight incubation, the cells are transfected using Lipofectamine-2000 (Invitrogen Corp.). The transfection mixture contain 2 μg of pCMV script PPAR-α, 4 μg of rat PPRE-pTAL-LUC, 1 μg of pAdvantage, 1 μg of pRL-CMV and 14 μl of Lipofectamine-2000. After five hours, the transfection medium is changed with minimum essential medium containing fetal bovine serum (without antibiotics) and cells are allowed to recover. After 24 hours transfected cells are trypsinised and replated in a 96 well NUNC-luminescence plate at a density of $3 \times 10^4$ cells per well. Cells are allowed to recover for twenty-four hours and then will expose to varying concentration of drug for 18-20 hours. After adding 70 μl of GLO-Lysis buffer (Invitrogen Corp.), cells are lysed by incubation at RT followed by repeat pipetting. From each well, 60 μl of the lysate are transferred to a new plate and to each well 75 μl of Dual-Glo substrate (Invitrogen Corp.) are added and plates are read as per manufacturers instructions. Reference: Frederikson et al., *J Lipid Res.,* 45: 592-601 (2004).

FXR Transactivation Assay: The assay is performed as described earlier by Cui et al (2003). Briefly $3.2 \times 10^4$ HepG2 cells are plated in 96-well plate and transfected with human full length FXR, human RXRα, human BSEP promoter construct and pCMV-lacZ constructs. Transfection mixture for each well contain 0.405 μl of FuGENE-6, 10.4 ng of pcDNA3.1-hFXR, 10.4 ng of pcDNA3.1-hRXRα, 10.4 ng of pGL3-enhancer-hBSEP-Promoter-Luc and 103.8 of pCMV-lacZ. The cells are then incubated for ~40-48 h in a fresh DMEM containing 5% CS-FBS with various concentrations of ligands. Cell lysates are produced using reporter lysis buffer (Promega) according to the manufacturer's directions. Luciferase and galactosidase activities in cell extracts are determined using Luciferase Assay Buffer (Promega) and β-D-galactopyranoside (Calbiochem) respectively. Reference: Cui et al., *J. Biol. Chem.,* 278:10214-10220 (2003).

CB1 Assay: CB1 assay is done according to the procedures as described by Rinaldi-Carmona et al. (1995). Membranes are isolated either from CHO cells over expressing either hCB1 or from the brain tissue according to standard procedures. Membranes are incubated with [$^3$H]-CP 55,940 (0.2 nM) in 1 ml of buffer A for 1 h. Membranes are harvested by rapid filtration technique using Whatman GF/C filters [preheated with 0.5% (w/v) polyethylenimine; Whatman, Clifton, N.J.], and a 48-well filtration apparatus (Brandel Inc., Gaithersburg, Md.). The labeled membranes are rinsed 3 times with 5 ml of cold buffer A containing 0.25% bovine serum albumin. The radioactivity is counted which bind to the filters with 4 ml of biofluor liquid scintillant. The non-specific binding is determined in the presence of 1 μM CP 55,940. Reference: Rinaldi-Carmona et al., *Life Sci.,* 56:1941-1947 (1995).

Assay Niacin binding: These receptors are cloned, over expressed and the membranes are prepared according to the procedure described by Zhang et al., (2005). Niacin binding assay is done by incubating the membranes with [3H]niacin at the appropriate concentrations of the membranes and the binding is assessed with a filter binding assay as described by Lorenzen et al., (2001). Reference: Zhang et al., *Biochem and Biophys. Res. Commun.,* 334:729-732 (2005), and Lorenzen et al., *Mol. Pharmacol.,* 59: 349-357 (2001).

Assay for DGAT2: Crude microsomal fractions are prepared for DGAT2 assay from murine livers. The synthesis of triacylglycerol from radioactive diacylglycerol is measured using crude microsomes as described by Dolinsky et al., (2004). A substrate suspension of 25 µM dioleoylglycerol (50000 d.p.m/assay) and 50 µM oleoyl-CoA is prepared by sonication in the assay buffer. The assay buffer contain 20 mM Tris/HCl, pH 7.4, 150 mM NaCl, 4 mM $MgCl_2$, 20 mM NaF, 1 mM dithiothreitol and 0.1% CHAPS. The reaction is initiated by the addition of microsomes (50 µg) to the assay mixture in a final volume of 200 µl. The reaction is proceeded for 10 min at 37° C. and is terminated by the addition of 4 µl of chloroform/methanol (2:1, v/v) and 750 µl of water. Samples are centrifuged at 1000 g for 10 min to separate organic and aqueous phases. The aqueous phase is removed and the organic phase is dried under nitrogen. Lipids are resuspended in 50 µl of chloroform/methanol (2:1, v/v) and spotted on a TLC plate. Lipids are separated in hexane/diethyl ether/acetic acid (80:20:1, by vol.) and visualize by staining in iodine vapour. Radioactive TAG is determined by scintillation counting. Reference: Dolinsky et al., *Bichem. J*, 378: 967-974 (2004).

Assay for CETP—CETP is a plasma protein and it transfers neutral lipids from high-density lipoprotein (HDL) to very low-density lipoprotein (VLDL). The CETP activity is measured by using Assay Kit from Biovision. A donor molecule containing a fluorescent neutral lipid is transferred to an acceptor molecule in the presence of CETP from a given plasma and serum sample. The fluorescent neutral lipid is present in a self-quenched state when contained within the core of the donor molecule. CETP-mediated transfer of the fluorescent neutral lipid to the acceptor molecule results in an increase in fluorescence (Excitation: 465; Emission: 535). Reference: Biovision Corporate, San Francisco, Calif., USA.

Reverse Transcription (RT-PCR) Assay: Gene expression profiling of normal and nutrient supplemented mouse brain samples are done for neuronal tyrosine/threonine phosphatase 1, microtubule associated α-AMPA-2, calcium and chloride channels, prolactin, transthyretin and transcription factor-NfiXi. The protocol is followed essentially as described by Watanabe et al. (2001), which involves the extraction of total RNA from normal, and diet supplemented animals brains using Trizol reagent further purified through RNeasy column. After extraction, total RNA would be converted into cDNA using random hexamers. The cDNA is quantified using real time PCR with fluorescent-labeled primers and probes of the gene of interest along with endogenous control for data normalization (TaqMan chemistry). Reference: Nakanishi K., *Bioorg. Med. Chem.*, 13: 4987-5000 (2005).

We claim:

1. A combination product or medicament comprising at least one substituted pyrrole derivative having the structure of Formula I,

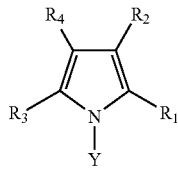

Formula I pharmaceutically acceptable salts, pharmaceutically acceptable solvates, prodrugs, metabolites, polymorphs, tautomers, racemates, pure enantiomers, diastereoisomers or N-oxides thereof, wherein:

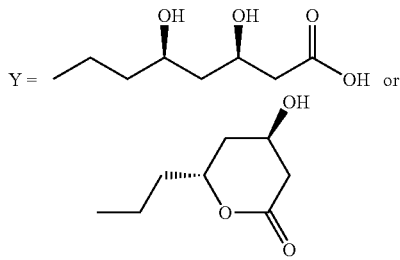

$R_1$ is $C_1$-$C_6$, or optionally substituted phenyl (wherein up to three substituents are independently selected from the group consisting of halogens, $C_1$-$C_6$ alkyl, cyano, or $C_1$-$C_3$ perfluoroalkyl;

$R_2$ is optionally substituted phenyl wherein up to three substituents are independently selected from the group consisting of cyano, acetyl, or optionally substituted amino, (wherein up to two amino substituents are independently selected from $C_1$-$C_6$ alkyl, $C_3$-$C_6$ cycloalkyl, acetyl, or sulfonamide);

$R_3$ is optionally substituted $C_1$-$C_6$ alkyl or $C_3$-$C_6$ cycloalkyl wherein the substituents are independently selected from the group consisting of halogens, hydroxyl, $C_1$-$C_3$ alkoxy and protected hydroxyl or —$NR_8R_9$, wherein $R_8$ and $R_9$ are optionally substituted $C_1$-$C_6$ alkyl wherein the optional substituent(s) is/are selected from halogens, hydroxy, $C_1$-$C_3$ alkoxy and protected hydroxyl;

$R_4$ is

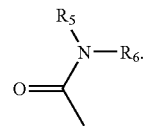

wherein $R_5$ and $R_6$ are independently hydrogen, $C_1$-$C_6$ alkyl or $C_3$-$C_6$ cycloalkyl, optionally substituted aryl or aralkyl, (wherein the substituents are selected from the group consisting of halogens, cyano, carboxy, optionally substituted $C_1$-$C_6$ alkyl wherein up to two substituents are independently selected from the group consisting of hydroxyl, protected hydroxyl, and halogen(s), and optionally substituted amino wherein up to two substituents are independently selected from the group consisting of $SO_2R_7$, $COR_7$, or $CONHR_7$, wherein $R_7$ is $C_1$-$C_6$ alkyl or aryl, or acetyl, trifluoromethyl, or $C_1$-$C_6$ alkoxycarbonyl, or $R_5$ and $R_6$ together form a 5-7 membered ring with one or more optional heteroatoms wherein the hetero atom(s) are independently selected from nitrogen, oxygen and sulfur, or $R_4$ is an optionally substituted mono-, bi- or tricyclic heterocycle having one or more hetero atom(s) wherein said hereto atom(s) is/are independently selected from oxygen, nitrogen and sulfur, and the optional substituents are independently selected from halogens, hydroxy, protected hydroxyl, $C_1$-$C_3$ alkoxy, cyano, $C_1$-$C_3$ perfluoroalkyl, $C_1$-$C_6$ alkyl or $C_3$-$C_6$ cycloalkyl, aryl or optionally substituted aralkyl wherein the substituents are independently selected from halogens, hydroxy, protected hydroxyl, $C_1$-$C_3$ alkoxy, cyano, or $C_1$-$C_3$ perfluoroalkyl, with the provisio that $R_2$ is phenyl only when (1) $R_5$ or $R_6$ is $C_3$-$C_6$ cycloalkyl or phenyl substituted with acetyl, alkyl, cycloalkyl, hydroxyalkyl, alkylsulfonamido, acetamido or (2) when $R_5$ and $R_6$ together form a 5-7 membered ring with or without one or more heteroatoms wherein the hetero atom(s) are selected from nitrogen, oxygen and sulfur or (3) when $R_5$ or $R_6$ is aralkyl optionally substituted with halogens, cyano, $C_1$-$C_6$ alkyl, $C_1$-$C_6$ halogenated alkyl or (4) when $R_4$ is optionally substituted mono-, bi- or tricyclic heterocycle having one or more hetero atom(s) wherein the optional substituents are independently selected from halogens, hydroxy, protected hydroxyl, $C_1$-$C_3$ alkoxy, cyano, perfluoroalkyl of one to three carbon atoms, $C_1$-$C_6$ alkyl, $C_3$-$C_6$ cycloalkyl, aryl, or optionally substituted aralkyl wherein the aralkyl substituents are independently selected from halogens hydroxy, protected hydroxyl, $C_1$-$C_3$ alkoxy, cyano, or $C_1$-$C_3$ perfluoroalkyl; and one or more dyslipidemic agents, antiobesity agents, antihyperglycaemic agents, anti-inflammatory agents or mixtures thereof.

2. The product or medicament according to claim 1, wherein:
(a) dyslipidemic agents are selected from cholesteryl ester transfer protein inhibitors, fibric acid derivatives/fibrates, antihypertensive agents, bile acid sequestrants, Acyl CoA -cholesterol acyltranferase inhibitors, cholesterol absorption inhibitors, bile acid reabsorption inhibitors, triglyceride synthesis inhibitors, MTP inhibitors, transcription modulators, squalene epoxidase inhibitors, LDL receptor inducers, platelet aggregation inhibitors, fish oils, omega 3 fatty acids, farnesoid X receptor agonists, liver X receptors, squalene synthase inhibitors, microsomal triglyceride and guggul lipids;
(b) antiobesity agents are selected from 5-HT reuptake inhibitors, pancreatic lipase inhibitors, cannabinoid antagonists and recombinant human ciliary neurotropic factors;
(c) antihyperglycaemic agents are selected from insulin sensitizing agents/PPAR agonists, sulphonyl ureas, alpha glucosidase inhibitors, DPP4 inhibitors and GLP-1 agonists; and
(d) anti-inflammatory agents are selected from β2 agonists, COX-2 inhibitors, 5-lipooxygenase inhibitors, phosphodiesterase IV inhibitors, MMP inhibitors, TNF-α inhibitors, caspase inhibitors, p38 mapkinase inhibitors, VLA-4 antagonists and PAF antagonists.

3. The product or medicament according to claim 2, wherein:
cholesteryl ester transfer protein inhibitors are selected from the group consisting of torcetrapib, JTT -705 and CP 532623;
fibric acid derivatives/fibrates are selected from the group consisting of etofibrate, fenofibrate, clofibrate, gemfibrozil, bezafibrate, ciprofibrate, clinofibrate and theofibrate;
antihypertensive agents are selected from the group consisting of amlodipine, its salts and prodrugs thereof, lomerizine, isradipine, lacidipine, lercadipine, manidipine, benidipine, cilnidipine, felodipine, bepridil, diltiazem, fendiline, nicardipine, nimodipine, nilvadipine, nitrendipine, nisoldipine, zonisamide and nifedipine;

bile acid sequestrants are selected from the group consisting of cholestyramine, colestipol, covesevelam, probucol and nicotinic acid;
Acyl CoA-cholesterol acyltranferase inhibitors are selected from the group consisting of F-12511 and NTE-122;
a cholesterol absorption inhibitor is ezetimibe;
MTP inhibitors are selected from the group consisting of batimastat (BB-94), marimastat (BB-2516), prinomastat (AG3340), BAY 12-9566 and CGS27023A;
5-HT reuptake inhibitors are selected from the group consisting of, femoxetine, fluoxetine, sertraline and sibutramine;
a pancreatic lipase inhibitor is orlistat;
a cannabinoid antagonist is rimonabant;
a recombinant human ciliary neurotropic factor is axokine;
insulin sensitizing agents/PPAR agonists are selected from the group consisting of pioglitazone, rosiglitazone, or muraglitazar;
a sulphonyl urea is metformin;
alpha glucosidase inhibitors are selected from the group consisting of acarbose, miglitol, miglustat and voglibose;
DPP4 inhibitors are selected from the group consisting of acarbose, miglitol, miglustat and voglibose;
GLP-1 agonists are selected from the group consisting of exendin-4, liraglutide and CJC-1131;
β2 agonists are selected from the group consisting of albuterol, formoterol, terbutaline and metaproterenol;
COX-2 inhibitors are selected from the group consisting of parecoxib, valdecoxib and rofecoxib;
5-lipooxygenase inhibitors are selected from the group consisting of zileuton and atreluton;
phosphodiesterase IV inhibitors are selected from the group consisting of RBx-11082, cilomilast and roflumilast;
MMP inhibitors are selected from the group consisting of batimastat (BB-94), marimastat (BB-2516), prinomastat (AG3340), BAY 12-9566 and CGS27023A;
TNF-α inhibitors are selected from the group consisting of infliximab, etanercept, D2E7 and CDP 571;
a caspase inhibitor is pralnacasan (Vx-740);
p38 mapkinase inhibitors are selected from the group consisting of Vx-745, BIRB-796, RWJ-67657 and SB-239063;
VLA-4 antagonists are selected from the group consisting of clafrinast and RBx-7796; and
PAF antagonists are selected from the group consisting of apafant, ibudilast, lexipafant, rupatadine, ginkgolides, and derivatives thereof.

4. The combination product or medicament of claim 1, wherein the at least one substituted pyrrole derivative and the one or more dyslipidemic agents, antiobesity agents, antihyperglycaemic agents, anti-inflammatory agents or mixtures thereof are formulated for separate administration.

5. The combination product or medicament of claim 1, wherein the at least one substituted pyrrole derivative and the one or more dyslipidemic agents, antiobesity agents, antihyperglycaemic agents, anti-inflammatory agents or mixtures thereof are formulated for simultaneous administration.

6. The combination product or medicament of claim 1, wherein the at least one substituted pyrrole derivative and the one or more dyslipidemic agents, antiobesity agents, antihyperglycaemic agents, anti-inflammatory agents or mixtures thereof are administered sequentially.

7. A method for the treatment of cardiovascular diseases, Alzheimer's disease, obesity, diabetes or inflammatory diseases comprising: administering to a mammal in need thereof a therapeutically effective amount of the combination product or medicament of claim 1.

8. The combination product or medicament of claim 1, wherein the at least one substituted pyrrole derivative is (3R, 5R)-7-[2-(4-fluorophenyl)-5-isopropyl-3-phenyl-4-[(4-hydroxymethylphenylamino)carbonyl]-pyrrol-1-yl]-3,5-dihydroxy-heptanoic acid

9. The combination product or medicament of claim 1, wherein the at least one substituted pyrrole derivative is (3R, 5R)-7-[2-(4-fluorophenyl)-5-isopropyl-3-phenyl-4-[4-carboxyphenyl)amino)carbonyl]-pyrrol-1-yl]-3,5-dihydroxy-heptanoic acid.

* * * * *